(12) United States Patent
Ramli et al.

(10) Patent No.: US 9,090,903 B2
(45) Date of Patent: Jul. 28, 2015

(54) β-KETOACYL ACP-SYNTHASE II (KASII) GENE FROM *JESSENIA BATAUA*

(75) Inventors: Umi Salamah Ramli, Selangor (MY); Ooi Kock Teh, Selangor (MY)

(73) Assignee: MALAYSIAN PALM OIL BOARD, Kajang, Selangor (MY)

( * ) Notice: Subject to any disclaimer, the term of this patent is extended or adjusted under 35 U.S.C. 154(b) by 361 days.

(21) Appl. No.: 13/478,209

(22) Filed: May 23, 2012

(65) Prior Publication Data
US 2013/0198904 A1    Aug. 1, 2013

(51) Int. Cl.
*C12N 15/82* (2006.01)
*C07H 21/04* (2006.01)
*C12N 9/10* (2006.01)

(52) U.S. Cl.
CPC .......... *C12N 15/8247* (2013.01); *C12N 9/1029* (2013.01); *C12Y 203/01041* (2013.01)

(58) Field of Classification Search
None
See application file for complete search history.

(56) References Cited

U.S. PATENT DOCUMENTS

| 5,500,361 A | 3/1996 | Kinney |
| 6,348,642 B1 | 2/2002 | Knauf et al. |
| 2004/0132189 A1 | 7/2004 | Dehesh |

OTHER PUBLICATIONS

Hahn 2002 (Molecular Phylogenetics and Evolution 23: p. 189-204).*
Nath et al 2009 (Theoretical and Applied Genetics 118: p. 765-773).*

* cited by examiner

*Primary Examiner* — Eileen B O Hara
*Assistant Examiner* — Matthew Keogh
(74) *Attorney, Agent, or Firm* — Kilpatrick Townsend & Stockton LLP

(57) ABSTRACT

The present invention relates to the use of a nucleic acid fragment or part thereof encoding β-ketoacyl ACP synthase II (KASII), particularly which derived from *Jessenia bataua* to enhance the production and the accumulation of very long chain fatty acids (VLCFA) in a plant, oil crops of particular.

11 Claims, 8 Drawing Sheets

```
                          -20              -10                0               10               20               30               40               50
                           |----|----|----|----|----|----|----|----|----|----|----|----|----|----|----|----|----|----|
SEQ ID NO:1        ....................--MAGAAVASPLCTWLVAACMT----VACDKEWPLG-PGSAS--PRR-----RWRRASLSGGVGRASPRRLLISAFCGA--
Eg                 -------------------.-MAGYSVAAPLCTWLVAACVT----ASGGKEGPLAAPGPAVGEARRLSRSARRRAAALRLDAPDSSGGLMSALRGPGI
Eo_ACQ41833        -------------------.--MSVTCAKENRTAPHAFHSSQPSNRLSRWARRRKTLHAQYNSDSSNSIAAGGGGGGGGGYSTEFLSNSLVSTLCGSSF
Jc_ABJ90469        -------------------MVGASSSYASPLCTWFVAACMS------VSHGGGDSRQAVALQSGGRSRRRRQLSKCSVASG------SASI
At_AAK69603        -------------------.--MASTTTSSLCTWLVAACMS-----VTCHADRTKTPHAMFRSSKKS--
Gm_AAW88763        -------------------.--MA--AVAGPLCTWLVAACLS----AACD--
Zm_ACG25173        -------------------.

60               70               80               90              100              110              120              130
                           |----|----|----|----|----|----|----|----|----|----|----|----|----|----|----|----|----|----|
SEQ ID NO:1        ---MSSCLAFEPCAEFYDSKGASAFFGESGFSLFGMWKAETTRRQRRAARAS--CVSGKAMAIAVQPAKEIAEKKRIHTK
Eg                 QGL.........S.RNG.....GD....L.RQN..........G..S.PSS.A..V.S......E.KV...E.TQ--
Eo_ACQ41833        QGL.........G.............T.........................V...................T...
Jc_ABJ90469        QGL........SQY.S.N.L----FRSR-----------NLN.KQR.LNRLAL..E.......E..V.T..KPA...
At_AAK69603        QALVT...D.G..THYNNNAL.SL..SNSV-----------SLN.NQR.LNRAAS..G...VMEM-E..A.VN.KPP.E
Gm_AAW88763        -------R..SQFNV-----CRS----------------TH....T..V.L..TQ..TTI.KPP.
Zm_ACG25173        -------AE..YKHKHCCPGGS.AG.GVML.---------Q.R.LG..RRGLAR..M...V.L.AERSVI...KPDI.

140              150              160              170              180              190              200              210
                           |----|----|----|----|----|----|----|----|----|----|----|----|----|----|----|----|----|----|
SEQ ID NO:1        KRRVVVTGMGVVTPLGDDPDIFYNLLDGVSGISQIETFDCTNYPTRIAGEIKSFSTDGLVAPKLSKRMDKFMLYLLIAG
Eg                 Q.................H...H..EE..K.....E.........SS............S.W..........T--
Eo_ACQ41833        ..............V.....................................
Jc_ABJ90469        Q.............S...HE..V....E........A.E.AQF.........WI...........M.T..
At_AAK69603        Q............E.S..H.HT..E...Q.N......SEF.........E.W............T..
Gm_AAW88763        Q.....L.......HE.............A......E....AE............W............M.T..
Zm_ACG25173        Q.............H...V................E.R...S.F..........W.V...A...........IT..
```

```
                460        470        480        490        500        510        520        530
                 |          |          |          |          |          |          |          |
SEQ ID NO:1 RCFGQNPELRVNSTKSMIGHLLGASGAVEAVAAIQAIRTGWVHPNINLENPEKSVDINVLVGSRKERLDVKVALSNSFGF
Eg          ...........................................................................K.G----.GWT.I.W--
Eo_ACQ41833 ....H....................A.....I...........V..............................
Jc_ABJ90469 ...........G........A.....TV........................DEG..T....PK...........
At_AAK69603 ....H....K..........A.G...T.........................DSG..TKL..PK....I.A....
Gm_AAW88763 ....H................................................DNG..AK...K......A....
Zm_ACG25173 ....R....Q...T..I..A.GI...S..............L..........DT..VGI..Q....CE......

540
                 |
SEQ ID NO:1 GGHNSSILFAPYK
Eg          QRRKDWM-----
Eo_ACQ41833 ........V...H.
Jc_ABJ90469 ........I.....
At_AAK69603 ........I.....
Gm_AAW88763 ..............
Zm_ACG25173 ........F.....
```

Figure 1 (cont'd)

SEQUENCE LISTING

```
<160> NUMBER OF SEQ ID NOS: 26

<210> SEQ ID NO 1
<211> LENGTH: 488
<212> TYPE: PRT
<213> ORGANISM: Jessenia bataua
<220> FEATURE:
<223> OTHER INFORMATION: beta-ketoacyl-acyl carrier protein (ACP)
      synthase (KASII)

<400> SEQUENCE: 1

Met Ser Ser Cys Leu Ala Phe Glu Pro Cys Ala Glu Phe Tyr Asp Ser
1               5                   10                  15

Lys Gly Ala Ser Ala Phe Phe Gly Glu Ser Gly Phe Ser Leu Phe Gly
            20                  25                  30

Met Trp Lys Ala Glu Thr Thr Arg Arg Gln Arg Arg Ala Ala Arg Ala
        35                  40                  45

Ser Cys Val Ser Gly Lys Ala Met Ala Ile Ala Val Gln Pro Ala Lys
    50                  55                  60

Glu Ile Ala Glu Lys Lys Arg Ile His Thr Lys Lys Arg Arg Val Val
65                  70                  75                  80

Val Thr Gly Met Gly Val Val Thr Pro Leu Gly Asp Asp Pro Asp Ile
                85                  90                  95

Phe Tyr Asn Asn Leu Leu Asp Gly Val Ser Gly Ile Ser Gln Ile Glu
            100                 105                 110

Thr Phe Asp Cys Thr Asn Tyr Pro Thr Arg Ile Ala Gly Glu Ile Lys
        115                 120                 125

Ser Phe Ser Thr Asp Gly Leu Val Ala Pro Lys Leu Ser Lys Arg Met
    130                 135                 140

Asp Lys Phe Met Leu Tyr Leu Leu Ile Ala Gly Lys Lys Ala Leu Ala
145                 150                 155                 160
```

Asn Gly Gly Ala Thr Glu Glu Val Met Ser Gln Leu Asp Lys Ala Lys
            165                 170                 175

Cys Gly Val Leu Ile Gly Ser Ala Met Gly Gly Met Lys Val Phe Asn
        180                 185                 190

Asp Ala Ile Glu Ala Leu Arg Val Ser Tyr Lys Lys Met Asn Pro Phe
    195                 200                 205

Cys Val Pro Phe Ala Thr Thr Asn Met Gly Ser Ala Ile Leu Ala Met
210                 215                 220

Asp Leu Gly Trp Met Gly Pro Asn Tyr Ser Ile Ser Thr Ala Cys Ala
225                 230                 235                 240

Thr Ser Asn Phe Cys Ile Leu Asn Ala Ala Asn His Ile Thr Arg Gly
                245                 250                 255

Glu Ala Asp Val Met Leu Cys Gly Gly Ser Asp Ala Ala Ile Ile Pro
            260                 265                 270

Ile Gly Leu Gly Gly Phe Val Ala Cys Arg Ala Leu Ser Gln Arg Asn
        275                 280                 285

Ser Asp Pro Thr Lys Ala Ser Arg Pro Trp Asp Val Asp Arg Asp Gly
    290                 295                 300

Phe Val Met Gly Glu Gly Ala Gly Val Leu Leu Leu Glu Glu Leu Glu
305                 310                 315                 320

His Ala Lys Gln Arg Gly Ala Asn Ile Tyr Ala Glu Phe Leu Gly Gly
                325                 330                 335

Ser Phe Thr Cys Asp Ala Tyr His Met Thr Glu Pro His Pro Glu Gly
            340                 345                 350

Ala Gly Ile Ala Leu Cys Ile Glu Asn Ala Leu Ala Gln Ala Gly Val
        355                 360                 365

Ala Lys Glu Asp Val Asn Tyr Val Asn Ala His Ala Thr Ser Thr Pro
    370                 375                 380

Ala Gly Asp Leu Lys Glu Tyr Gln Ala Leu Ile Arg Cys Phe Gly Gln
385                 390                 395                 400

Asn Pro Glu Leu Arg Val Asn Ser Thr Lys Ser Met Ile Gly His Leu
                405                 410                 415

Leu Gly Ala Ser Gly Ala Val Glu Ala Val Ala Ala Ile Gln Ala Ile
            420                 425                 430

Arg Thr Gly Trp Val His Pro Asn Ile Asn Leu Glu Asn Pro Glu Lys
        435                 440                 445

Ser Val Asp Ile Asn Val Leu Val Gly Ser Arg Lys Glu Arg Leu Asp
    450                 455                 460

Val Lys Val Ala Leu Ser Asn Ser Phe Gly Phe Gly Gly His Asn Ser
465                 470                 475                 480

Ser Ile Leu Phe Ala Pro Tyr Lys
                485

<210> SEQ ID NO 2
<211> LENGTH: 1872
<212> TYPE: DNA
<213> ORGANISM: Jessenia bataua
<220> FEATURE:
<223> OTHER INFORMATION: beta-ketoacyl-acyl carrier protein (ACP)
      synthase (KASII) nucleic acid fragment
<220> FEATURE:
<221> NAME/KEY: CDS
<222> LOCATION: (229)...(1696)
<223> OTHER INFORMATION: KASII

<400> SEQUENCE: 2

-continued

| | |
|---|---|
| gggagatggg aggcggggcg cgccgctctg ccgtggttgg tggcggcgtg cgtgacggcg | 60 |
| tcgggcggaa aggaggggcc tttggcagcg ccggcgcccg cggtcgggga ggggaggcgg | 120 |
| ctgagccggt cggcgaggag gcggagggcg gcggcgctcc gacttgacgc gcgggattcc | 180 |
| tccgggggtc tagtgtcagc gctccgtgga tcggggatcc aggggctgat gagctcctgc | 240 |
| ctcgccttcg agccctgcgc ggagttctac gactctaagg gtgcgtcggc gttcttcggg | 300 |
| gagagtggct tctccctctt tgggatgtgg aaggcggaga ctacgagaag gcagcgaagg | 360 |
| gccgcgcgcg catcttgcgt ctcgggcaag gcaatggcaa tagctgtgca gcctgctaaa | 420 |
| gaaattgcag aaaagaagag aatccataca aagaagagga gggtggtcgt gactgggatg | 480 |
| ggtgtggtga ctccactggg cgatgatcct gatatcttct acaataacct tcttgatggt | 540 |
| gtcagtggta taagtcaaat tgaaacattt gactgtacaa actatccaac aagaattgca | 600 |
| ggagaaatta aatctttctc aacggatgga ttggtggcac taaattatc taaacgaatg | 660 |
| gacaaattca tgctctattt acttattgct ggaaagaaag cattagccaa tggtggggct | 720 |
| acagaagagg tcatgagtca gcttgacaag gcaaaatgcg gggtgctcat aggctctgca | 780 |
| atgggtggaa tgaaggtttt taatgatgcc atcgaagctt taagggtctc atataagaag | 840 |
| atgaatccat tttgtgttcc atttgcaacg acaaacatgg ttctgcaat ccttgctatg | 900 |
| gatctggggt ggatgggccc aaattactct atttcaactg cttgtgctac aagcaatttc | 960 |
| tgtatcctga atgcagcaaa ccatataaca agaggggaag cggatgtgat gctttgtggt | 1020 |
| ggatcagatg ccgcaattat acccattgga ctgggggggtt tgttgcttg cagagcactt | 1080 |
| tcacagagaa atagtgatcc gactaaagca tcgcgcccctt gggacgttga tcgtgatgga | 1140 |
| tttgtgatgg gggaaggggc tggtgtgctt ctactggaag aattagagca tgctaagcaa | 1200 |
| agaggagcga atatctatgc tgaatttctt ggaggaagct tcacgtgtga tgcttaccac | 1260 |
| atgactgagc cacatcctga gggggcaggc attgctcttt gcattgagaa tgcattagcg | 1320 |
| caagcagggg tagccaaaga agatgttaat tatgtaaatg ctcatgcaac ttcaacacct | 1380 |
| gctggtgatc taaaagagta tcaagctctc attcgttgtt ttgggcagaa tcctgagctg | 1440 |
| agagtgaact ctacaaaatc catgattggt cacctactag gagcttctgg tgcggtggaa | 1500 |
| gctgttgctg caattcaggc aattcgaaca gggtgggtcc atccaaatat caatctcgaa | 1560 |
| aacccagaaa aaagtgtgga tataaatgtg ctggtgggct cgagaaagga aaggttggat | 1620 |
| gtgaaggtgg cactatcaaa ctcattcggt tttggtggcc acaactcgtc tatcttattt | 1680 |
| gcaccttaca aatagtcatg gaatgaactt cagatgttaa aaggatagca tttagcccag | 1740 |
| cttcttttgtt ggtttccaag atcatctcaa gaattccaag ccatggtttt gcttagcttg | 1800 |
| caaccaggcc cgtgattgtt gtgtggggct catttgtttt tggtgggtta tctcttgaaa | 1860 |
| gactcatttc tt | 1872 |

<210> SEQ ID NO 3
<211> LENGTH: 54
<212> TYPE: DNA
<213> ORGANISM: Artificial Sequence
<220> FEATURE:
<223> OTHER INFORMATION: synthetic PCR GeneRacer oligo dT primer

<400> SEQUENCE: 3

| | |
|---|---|
| gctgtcaacg atacgctacg taacggcatg acagtgtttt tttttttttt tttt | 54 |

<210> SEQ ID NO 4
<211> LENGTH: 19

-continued

```
<212> TYPE: DNA
<213> ORGANISM: Artificial Sequence
<220> FEATURE:
<223> OTHER INFORMATION: synthetic 3' RACE PCR primary primer GSP 1

<400> SEQUENCE: 4
gccacatctg aaggtagag                                                19

<210> SEQ ID NO 5
<211> LENGTH: 20
<212> TYPE: DNA
<213> ORGANISM: Artificial Sequence
<220> FEATURE:
<223> OTHER INFORMATION: synthetic 3' RACE PCR amplification nested
      primer GSP 2

<400> SEQUENCE: 5
tgagttatgc ccaccgcctc                                               20

<210> SEQ ID NO 6
<211> LENGTH: 28
<212> TYPE: DNA
<213> ORGANISM: Artificial Sequence
<220> FEATURE:
<223> OTHER INFORMATION: synthetic 5' RACE PCR amplification primer
      GSP 3

<400> SEQUENCE: 6
caccagatgg tgttgaagtt gcatgagc                                      28

<210> SEQ ID NO 7
<211> LENGTH: 28
<212> TYPE: DNA
<213> ORGANISM: Artificial Sequence
<220> FEATURE:
<223> OTHER INFORMATION: synthetic 5' RACE PCR amplification primer
      GSP 4

<400> SEQUENCE: 7
cctgattctg ctagcgcctt ctcaatgc                                      28

<210> SEQ ID NO 8
<211> LENGTH: 35
<212> TYPE: DNA
<213> ORGANISM: Artificial Sequence
<220> FEATURE:
<223> OTHER INFORMATION: synthetic amplification primer BamHI-KasF

<400> SEQUENCE: 8
ggatccatga gctcctgcct cgccttcgag ccctg                              35

<210> SEQ ID NO 9
<211> LENGTH: 38
<212> TYPE: DNA
<213> ORGANISM: Artificial Sequence
<220> FEATURE:
<223> OTHER INFORMATION: synthetic amplification primer Not1-KasR

<400> SEQUENCE: 9
gcggcggcat ttgtaaggtg caaataagat agacgagt                           38

<210> SEQ ID NO 10
<211> LENGTH: 33
<212> TYPE: DNA
<213> ORGANISM: Artificial Sequence
<220> FEATURE:
<223> OTHER INFORMATION: synthetic GFP-specific primer BamHI-GFP6-F
```

```
<400> SEQUENCE: 10
cggatcccca tgagtaaagg agaactttc act                                33

<210> SEQ ID NO 11
<211> LENGTH: 34
<212> TYPE: DNA
<213> ORGANISM: Artificial Sequence
<220> FEATURE:
<223> OTHER INFORMATION: synthetic GFP-specific primer EcoRI-GFP6-R

<400> SEQUENCE: 11
cgaattccct ttgtatagtt catccatgcc atgt                              34

<210> SEQ ID NO 12
<211> LENGTH: 24
<212> TYPE: DNA
<213> ORGANISM: Artificial Sequence
<220> FEATURE:
<223> OTHER INFORMATION: synthetic gene-specific primer gKASF4

<400> SEQUENCE: 12
tgaggagaag gatataaatg ggca                                         24

<210> SEQ ID NO 13
<211> LENGTH: 27
<212> TYPE: DNA
<213> ORGANISM: Artificial Sequence
<220> FEATURE:
<223> OTHER INFORMATION: synthetic gene-specific primer gKASF6

<400> SEQUENCE: 13
tctattctct ccttctcttc tttctcc                                      27

<210> SEQ ID NO 14
<211> LENGTH: 30
<212> TYPE: DNA
<213> ORGANISM: Artificial Sequence
<220> FEATURE:
<223> OTHER INFORMATION: synthetic reverse primer gKASR6

<400> SEQUENCE: 14
acctttgcat cattcagcta gaagtaaaac                                   30

<210> SEQ ID NO 15
<211> LENGTH: 30
<212> TYPE: DNA
<213> ORGANISM: Artificial Sequence
<220> FEATURE:
<223> OTHER INFORMATION: synthetic amplification primer JkasCF

<400> SEQUENCE: 15
gcdtgatttc ttcgaggagg aagcttcacg                                   30

<210> SEQ ID NO 16
<211> LENGTH: 27
<212> TYPE: DNA
<213> ORGANISM: Artificial Sequence
<220> FEATURE:
<223> OTHER INFORMATION: synthetic amplification primer JkasCR

<400> SEQUENCE: 16
cacatccaac ctttcctttc tcgagcc                                      27

<210> SEQ ID NO 17
```

```
<211> LENGTH: 27
<212> TYPE: DNA
<213> ORGANISM: Artificial Sequence
<220> FEATURE:
<223> OTHER INFORMATION: synthetic primer JkasNF

<400> SEQUENCE: 17
ggcgatgatc ctgatatctt ctacaat                                        27

<210> SEQ ID NO 18
<211> LENGTH: 27
<212> TYPE: DNA
<213> ORGANISM: Artificial Sequence
<220> FEATURE:
<223> OTHER INFORMATION: synthetic primer JkasNR

<400> SEQUENCE: 18
aacgtcccaa gggcgcgatg ctttagc                                        27

<210> SEQ ID NO 19
<211> LENGTH: 24
<212> TYPE: DNA
<213> ORGANISM: Artificial Sequence
<220> FEATURE:
<223> OTHER INFORMATION: synthetic primer JK3UTRF

<400> SEQUENCE: 19
catggaatga acttcagatg ttaa                                           24

<210> SEQ ID NO 20
<211> LENGTH: 26
<212> TYPE: DNA
<213> ORGANISM: Artificial Sequence
<220> FEATURE:
<223> OTHER INFORMATION: synthetic primer JK3UTRR

<400> SEQUENCE: 20
aaaagaaatg agtccttcaa gagaat                                         26

<210> SEQ ID NO 21
<211> LENGTH: 537
<212> TYPE: PRT
<213> ORGANISM: Elaeis guineensis
<220> FEATURE:
<223> OTHER INFORMATION: African oil palm (Eg) beta-ketoacyl-acyl
      carrier protein (ACP) synthase (KASII)

<400> SEQUENCE: 21
```

Met Ala Gly Ala Ala Val Ala Ser Pro Leu Cys Thr Trp Leu Val Ala
1               5                   10                  15

Ala Cys Met Thr Val Ala Cys Asp Lys Glu Trp Pro Leu Gly Pro Gly
            20                  25                  30

Ser Ala Ser Pro Arg Arg Trp Arg Arg Ala Ser Leu Ser Gly Gly
        35                  40                  45

Val Gly Arg Ala Ser Pro Arg Arg Leu Ile Ser Ala Phe Cys Gly Ala
    50                  55                  60

Gln Gly Leu Met Ser Ser Cys Leu Ala Phe Glu Pro Cys Ala Glu Phe
65                  70                  75                  80

Tyr Ser Ser Arg Asn Gly Ser Ala Phe Phe Gly Gly Asp Gly Phe Ser
                85                  90                  95

Leu Leu Gly Arg Gln Asn Ala Glu Thr Thr Arg Arg Gln Arg Gly
            100                 105                 110

Ala Arg Ser Ser Pro Ser Ser Val Ala Gly Lys Val Met Ser Ile Ala

-continued

```
            115                 120                 125
Ala Val Gln Pro Glu Lys Lys Val Ala Glu Lys Glu Arg Thr Gln Gln
    130                 135                 140
Arg Arg Val Val Val Thr Gly Met Gly Val Thr Pro Leu Gly His
145                 150                 155                 160
Asp Pro Asp His Phe Tyr Glu Glu Leu Leu Lys Gly Val Ser Gly Ile
                    165                 170                 175
Ser Glu Ile Glu Thr Phe Asp Cys Ser Ser Tyr Pro Thr Arg Ile Ala
                180                 185                 190
Gly Glu Ile Lys Ser Phe Ser Ser Asp Gly Trp Val Ala Pro Lys Leu
                195                 200                 205
Ser Lys Arg Met Asp Lys Phe Met Leu Tyr Leu Leu Thr Lys Lys Ala
    210                 215                 220
Leu Glu Asn Gly Gly Leu Thr Glu Glu Ala Met Ser Trp Leu Asp Lys
225                 230                 235                 240
Glu Arg Cys Gly Val Leu Ile Gly Ser Ala Met Gly Gly Met Lys Val
                    245                 250                 255
Phe Asn Asp Ala Ile Glu Ala Leu Arg Ile Ser Tyr Lys Lys Met Asn
                260                 265                 270
Pro Phe Cys Val Pro Phe Ala Thr Thr Asn Met Gly Ser Ala Met Leu
                275                 280                 285
Ala Met Asp Leu Gly Trp Met Gly Pro Asn Tyr Ser Thr Ala Cys Ala
                290                 295                 300
Thr Ser Asn Phe Cys Ile Leu Asn Ala Ala Asn His Ile Ile Arg Asp
305                 310                 315                 320
Glu Ala Asp Val Met Leu Cys Gly Gly Ser Asp Ala Ala Ile Ile Pro
                    325                 330                 335
Ile Gly Leu Gly Gly Phe Val Ala Cys Gly Ala Leu Ser Gln Arg Asn
                340                 345                 350
Ser Asp Pro Thr Lys Ala Ser Arg Pro Trp Asp Ile Asp Arg Asp Gly
                355                 360                 365
Phe Val Met Gly Glu Gly Ala Gly Val Leu Glu Glu Leu Glu His Ala
                370                 375                 380
Lys Gln Arg Gly Ala Asn Ile Tyr Ala Glu Phe Leu Gly Gly Ser Phe
385                 390                 395                 400
Thr Cys Asp Ala Tyr His Met Thr Glu Pro His Pro Glu Gly Ala Gly
                    405                 410                 415
Ile Ala Leu Cys Ile Glu Asn Ala Leu Ala Gln Ala Gly Val Ala Lys
                420                 425                 430
Glu Asp Val Asn Tyr Val Asn Ala His Ala Thr Ser Thr Pro Ala Gly
                435                 440                 445
Asp Leu Lys Glu Tyr Gln Ala Arg Cys Phe Gly Gln Asn Pro Glu Leu
                450                 455                 460
Arg Val Asn Ser Thr Lys Ser Met Ile Gly His Leu Leu Gly Ala Ser
465                 470                 475                 480
Gly Ala Val Glu Ala Val Ala Ala Ile Gln Ala Ile Arg Thr Gly Trp
                    485                 490                 495
Val His Pro Asn Val Asn Leu Glu Asn Pro Glu Lys Ser Val Asp Ile
                500                 505                 510
Asn Val Leu Val Gly Ser Lys Lys Gly Lys Gly Trp Thr Thr Ser Ile
                515                 520                 525
Ser Trp Gln Arg Arg Lys Asp Trp Met
                530                 535
```

<210> SEQ ID NO 22
<211> LENGTH: 562
<212> TYPE: PRT
<213> ORGANISM: Elaeis oleifera
<220> FEATURE:
<223> OTHER INFORMATION: American oil palm (Eo) beta-ketoacyl-acyl carrier protein (ACP) synthase (KASII, KAS-II), polyketide synthase

<400> SEQUENCE: 22

```
Met Ala Gly Tyr Ser Val Ala Ala Pro Leu Cys Thr Trp Leu Val Ala
 1               5                  10                  15

Ala Cys Val Thr Ala Ser Gly Gly Lys Glu Gly Pro Leu Ala Ala Pro
            20                  25                  30

Gly Pro Ala Val Gly Glu Ala Arg Arg Leu Ser Arg Ser Ala Arg Arg
        35                  40                  45

Arg Arg Ala Ala Ala Leu Arg Leu Asp Ala Arg Asp Ser Ser Gly Gly
    50                  55                  60

Leu Met Ser Ala Leu Arg Gly Pro Gly Ile Gln Gly Leu Met Ser Ser
65                  70                  75                  80

Cys Leu Ala Phe Glu Pro Cys Ala Glu Phe Tyr Gly Ser Lys Gly Ala
                85                  90                  95

Ser Ala Phe Phe Gly Glu Ser Gly Phe Ser Leu Phe Gly Thr Trp Lys
            100                 105                 110

Ala Glu Thr Thr Arg Arg Gln Arg Arg Ala Ala Arg Ala Ser Cys Val
        115                 120                 125

Ser Gly Lys Ala Met Ala Val Ala Val Gln Pro Ala Lys Glu Ile Ala
    130                 135                 140

Glu Lys Lys Arg Thr His Thr Lys Lys Arg Arg Val Val Val Thr Gly
145                 150                 155                 160

Met Gly Val Val Thr Pro Leu Gly Val Asp Pro Asp Ile Phe Tyr Asn
                165                 170                 175

Asn Leu Leu Asp Gly Val Ser Gly Ile Ser Gln Ile Glu Thr Phe Asp
            180                 185                 190

Cys Thr Asn Tyr Pro Thr Arg Ile Ala Gly Glu Ile Lys Ser Phe Ser
        195                 200                 205

Thr Asp Gly Leu Val Ala Pro Lys Leu Ser Lys Arg Met Asp Lys Phe
    210                 215                 220

Met Leu Tyr Leu Leu Ile Ala Gly Lys Lys Ala Leu Ala Asn Gly Gly
225                 230                 235                 240

Val Thr Glu Glu Val Met Ser Gln Leu Asp Lys Ala Lys Cys Gly Val
                245                 250                 255

Leu Ile Gly Ser Ala Met Gly Gly Met Lys Val Phe Asn Asp Ala Ile
            260                 265                 270

Glu Ala Leu Arg Val Ser Tyr Lys Lys Met Asn Pro Phe Cys Val Pro
        275                 280                 285

Phe Ala Thr Thr Asn Met Gly Ser Ala Ile Leu Ala Met Asp Leu Gly
    290                 295                 300

Trp Met Gly Pro Asn Tyr Ser Ile Ser Thr Ala Cys Ala Thr Ser Asn
305                 310                 315                 320

Phe Cys Ile Leu Asn Ala Ala Asn His Ile Ile Arg Arg Glu Ala Asp
                325                 330                 335

Val Met Leu Cys Gly Gly Ser Asp Ala Ala Ile Ile Pro Leu Thr Gly
            340                 345                 350
```

```
Gly Phe Val Leu Ala Glu His Ser Arg Arg Glu Ile Val Ile Arg Leu
            355                 360                 365

Lys Arg His Gly Pro Trp Asp Ile Asp Arg Asp Gly Phe Val Met Gly
370                 375                 380

Glu Gly Ala Gly Val Leu Leu Leu Glu Glu Leu Glu His Ala Lys Gln
385                 390                 395                 400

Arg Gly Ala Asn Ile Tyr Ala Glu Phe Leu Gly Gly Ser Phe Thr Cys
            405                 410                 415

Asp Ala Tyr His Met Thr Glu Pro His Pro Glu Gly Ile Ala Leu Cys
            420                 425                 430

Ile Glu Asn Ala Leu Ala Gln Ala Gly Val Ala Lys Glu Asp Val Asn
            435                 440                 445

Tyr Val Asn Ala His Ala Thr Ser Thr Pro Ala Gly Asp Leu Lys Glu
        450                 455                 460

Tyr Gln Ala Leu Ile Arg Cys Phe Gly Gln Asn Pro Glu Leu Arg Val
465                 470                 475                 480

Asn Ser Thr Lys Ser Met Ile Gly His Leu Leu Gly Ala Ser Gly Ala
            485                 490                 495

Val Glu Ala Val Ala Ala Ile Gln Ala Ile Arg Thr Gly Trp Val His
                500                 505                 510

Pro Asn Val Asn Leu Glu Asn Pro Glu Lys Ser Val Asp Ile Asn Val
            515                 520                 525

Leu Val Gly Ser Arg Lys Glu Arg Leu Asp Val Lys Val Ala Leu Ser
            530                 535                 540

Asn Ser Phe Gly Phe Gly Gly His Asn Ser Ser Ile Leu Phe Ala Pro
545                 550                 555                 560

Tyr Lys

<210> SEQ ID NO 23
<211> LENGTH: 554
<212> TYPE: PRT
<213> ORGANISM: Jatropha curcas
<220> FEATURE:
<223> OTHER INFORMATION: Barbados nut (purging nut, physic nut, Jc)
      beta-ketoacyl-acyl carrier protein (ACP) synthase (KASII)

<400> SEQUENCE: 23

Met Ser Val Thr Cys Ala Lys Glu Asn Arg Thr Ala Pro His Ala Phe
1               5                   10                  15

His Ser Ser Gln Pro Ser Asn Arg Leu Ser Arg Trp Ala Arg Arg Arg
            20                  25                  30

Lys Thr Leu His Ala Gln Tyr Asn Ser Asp Ser Ser Asn Ser Ile Ala
        35                  40                  45

Ala Gly Gly Gly Gly Gly Gly Gly Tyr Ser Thr Glu Phe Leu
50                  55                  60

Ser Asn Ser Leu Val Ser Thr Leu Cys Gly Ser Ser Phe Gln Gly Leu
65                  70                  75                  80

Met Ser Ser Cys Leu Ala Phe Glu Pro Cys Ser Gln Tyr Tyr Ser Ser
            85                  90                  95

Asn Gly Leu Phe Arg Ser Arg Asn Leu Asn Arg Lys Gln Arg Arg Leu
            100                 105                 110

Asn Arg Leu Ala Leu Ser Gly Glu Ala Met Ala Ile Ala Val Gln Pro
        115                 120                 125

Glu Lys Glu Val Ala Thr Lys Lys Pro Ala Thr Lys Gln Arg Arg
        130                 135                 140
```

```
Val Val Val Thr Gly Met Gly Val Val Ser Pro Leu Gly His Glu Pro
145                 150                 155                 160

Asp Val Phe Tyr Asn Asn Leu Leu Glu Gly Val Ser Gly Ile Ser Gln
                165                 170                 175

Ile Glu Ala Phe Glu Cys Ala Gln Phe Pro Thr Arg Ile Ala Gly Glu
            180                 185                 190

Ile Lys Ser Phe Ser Thr Asp Gly Trp Ile Ala Pro Lys Leu Ser Lys
        195                 200                 205

Arg Met Asp Lys Phe Met Leu Tyr Met Leu Thr Ala Gly Lys Lys Ala
    210                 215                 220

Leu Ala Asp Gly Gly Ile Thr Glu Asp Ile Met Asp Glu Leu Asp Lys
225                 230                 235                 240

Ala Lys Cys Gly Val Leu Ile Gly Ser Ala Met Gly Gly Met Lys Val
                245                 250                 255

Phe Asn Asp Ala Ile Glu Ala Leu Arg Val Ser Tyr Arg Lys Met Asn
                260                 265                 270

Pro Phe Cys Val Pro Phe Ala Thr Thr Asn Met Gly Ser Ala Met Leu
            275                 280                 285

Ala Met Asp Leu Gly Trp Met Gly Pro Asn Tyr Ser Ile Ser Thr Ala
290                 295                 300

Cys Ala Thr Ser Asn Phe Cys Ile Leu Asn Ala Ala Asn His Ile Ile
305                 310                 315                 320

Arg Gly Glu Ala Asp Ile Met Leu Cys Gly Gly Ser Asp Ala Ala Ile
                325                 330                 335

Ile Pro Ile Gly Leu Gly Gly Phe Val Ala Cys Arg Ala Leu Ser Gln
            340                 345                 350

Arg Asn Asp Asp Pro Ala Lys Ala Ser Arg Pro Trp Asp Met Asn Arg
        355                 360                 365

Asp Gly Phe Val Met Gly Glu Gly Ala Gly Val Leu Leu Leu Glu Glu
    370                 375                 380

Leu Glu His Ala Lys Lys Arg Gly Ala Asn Ile Tyr Ala Glu Phe Leu
385                 390                 395                 400

Gly Gly Ser Phe Thr Cys Asp Ala Tyr His Met Thr Glu Pro Arg Pro
                405                 410                 415

Gly Gly Ile Gly Val Ile Leu Cys Val Glu Lys Ala Leu Ala Gln Ser
            420                 425                 430

Gly Val Ser Arg Glu Asp Val Asn Tyr Ile Asn Ala His Ala Thr Ser
        435                 440                 445

Thr Pro Ala Gly Asp Ile Lys Glu Phe Gly Ala Leu Met His Cys Phe
    450                 455                 460

Gly Gln Asn Pro Gly Leu Arg Val Asn Ser Thr Lys Ser Met Ile Gly
465                 470                 475                 480

His Leu Leu Gly Ala Ala Gly Ala Val Glu Ala Ile Ala Ala Ile Gln
                485                 490                 495

Ala Ile Arg Thr Gly Trp Val His Pro Asn Ile Asn Leu Glu Asn Pro
            500                 505                 510

Asp Glu Gly Val Asp Thr Asn Val Leu Val Gly Pro Lys Lys Glu Arg
        515                 520                 525

Leu Asp Val Lys Val Ala Leu Ser Asn Ser Phe Gly Phe Gly Gly His
    530                 535                 540

Asn Ser Ser Ile Val Phe Ala Pro His Lys
545                 550
```

-continued

```
<210> SEQ ID NO 24
<211> LENGTH: 541
<212> TYPE: PRT
<213> ORGANISM: Arabidopsis thaliana
<220> FEATURE:
<223> OTHER INFORMATION: thale cress (Ar) ecotype Wassilewskija
      beta-ketoacyl-acyl carrier protein (ACP) synthase
      (KASII), condensing enzyme

<400> SEQUENCE: 24
```

| | | | | | | | | | | | | | | |
|---|---|---|---|---|---|---|---|---|---|---|---|---|---|---|
|Met|Val|Gly|Ala|Ser|Ser|Tyr|Ala|Ser|Pro|Leu|Cys|Thr|Trp|Phe|
|1| | | |5| | | | |10| | | | |15|
|Val|Ala|Ala|Cys|Met|Ser|Val|Ser|His|Gly|Gly|Gly|Asp|Ser|Arg|Gln|
| | | |20| | | | |25| | | | |30| | |
|Ala|Val|Ala|Leu|Gln|Ser|Gly|Gly|Arg|Ser|Arg|Arg|Arg|Gln|Leu|
| | |35| | | | |40| | | | |45| | |
|Ser|Lys|Cys|Ser|Val|Ala|Ser|Gly|Ser|Ala|Ser|Ile|Gln|Ala|Leu|Val|
| |50| | | | |55| | | | |60| | | | |
|Thr|Ser|Cys|Leu|Asp|Phe|Gly|Pro|Cys|Thr|His|Tyr|Asn|Asn|Asn|Asn|
|65| | | | |70| | | | |75| | | | |80|
|Ala|Leu|Ser|Ser|Leu|Phe|Gly|Ser|Asn|Ser|Val|Ser|Leu|Asn|Arg|Asn|
| | | | |85| | | | |90| | | | |95| |
|Gln|Arg|Arg|Leu|Asn|Arg|Ala|Ala|Ser|Ser|Gly|Gly|Ala|Met|Ala|Val|
| | | |100| | | | |105| | | | |110| | |
|Met|Glu|Met|Glu|Lys|Glu|Ala|Ala|Val|Asn|Lys|Lys|Pro|Pro|Thr|Glu|
| | |115| | | | |120| | | | |125| | | |
|Gln|Arg|Arg|Val|Val|Val|Thr|Gly|Met|Gly|Val|Glu|Thr|Ser|Leu|Gly|
| |130| | | | |135| | | | |140| | | | |
|His|Asp|Pro|His|Thr|Phe|Tyr|Glu|Asn|Leu|Leu|Gln|Gly|Asn|Ser|Gly|
|145| | | | |150| | | | |155| | | | |160|
|Ile|Ser|Gln|Ile|Glu|Asn|Phe|Asp|Cys|Ser|Glu|Phe|Pro|Thr|Arg|Ile|
| | | | |165| | | | |170| | | | |175| |
|Ala|Gly|Glu|Ile|Lys|Ser|Phe|Ser|Thr|Glu|Gly|Trp|Val|Ala|Pro|Lys|
| | | |180| | | | |185| | | | |190| | |
|Leu|Ser|Lys|Arg|Met|Asp|Lys|Phe|Met|Leu|Tyr|Leu|Leu|Thr|Ala|Gly|
| | |195| | | | |200| | | | |205| | | |
|Lys|Lys|Ala|Leu|Ala|Asp|Gly|Gly|Val|Thr|Asp|Glu|Val|Met|Ala|Glu|
| |210| | | | |215| | | | |220| | | | |
|Phe|Asp|Lys|Thr|Lys|Cys|Gly|Val|Leu|Ile|Gly|Ser|Ala|Met|Gly|Gly|
|225| | | | |230| | | | |235| | | | |240|
|Met|Lys|Val|Phe|Tyr|Asp|Ala|Ile|Glu|Ala|Leu|Arg|Ile|Ser|Tyr|Lys|
| | | | |245| | | | |250| | | | |255| |
|Lys|Met|Asn|Pro|Phe|Cys|Val|Pro|Phe|Ala|Thr|Thr|Asn|Met|Gly|Ser|
| | | |260| | | | |265| | | | |270| | |
|Ala|Met|Leu|Ala|Met|Asp|Leu|Gly|Trp|Met|Gly|Pro|Asn|Tyr|Ser|Ile|
| | |275| | | | |280| | | | |285| | | |
|Ser|Thr|Ala|Cys|Ala|Thr|Ser|Asn|Phe|Cys|Ile|Leu|Asn|Ser|Ala|Asn|
| |290| | | | |295| | | | |300| | | | |
|His|Ile|Ile|Lys|Gly|Glu|Ala|Asp|Val|Met|Leu|Cys|Gly|Gly|Ser|Asp|
|305| | | | |310| | | | |315| | | | |320|
|Ala|Val|Ile|Ile|Pro|Ile|Gly|Leu|Gly|Gly|Phe|Val|Ala|Cys|Arg|Ala|
| | | | |325| | | | |330| | | | |335| |
|Leu|Ser|Gln|Arg|Asn|Asn|Asp|Pro|Thr|Lys|Ala|Ser|Arg|Pro|Trp|Asp|
| | | |340| | | | |345| | | | |350| | |
|Thr|Asn|Arg|Asp|Gly|Phe|Val|Met|Gly|Glu|Gly|Ala|Gly|Val|Leu|Leu|
| | |355| | | | |360| | | | |365| | | |

```
Leu Glu Glu Leu Glu His Ala Lys Lys Arg Gly Ala Thr Ile Tyr Ala
    370                 375                 380

Glu Phe Leu Gly Gly Ser Phe Thr Cys Asp Ala Tyr His Met Thr Glu
385                 390                 395                 400

Pro His Pro Asp Gly Ala Gly Val Ile Leu Cys Ile Glu Arg Ala Leu
                405                 410                 415

Ala Ser Ala Gly Ile Ser Lys Glu Gln Ile Asn Tyr Ile Asn Ala His
            420                 425                 430

Ala Thr Ser Thr His Ala Gly Asp Ile Lys Glu Tyr Gln Ala Leu Ala
            435                 440                 445

His Cys Phe Gly Gln Asn Pro Glu Leu Lys Val Asn Ser Thr Lys Ser
    450                 455                 460

Met Ile Gly His Leu Leu Gly Ala Ala Gly Ala Val Glu Ala Val Ala
465                 470                 475                 480

Thr Val Gln Ala Ile Arg Thr Gly Trp Val His Pro Asn Ile Asn Leu
                485                 490                 495

Glu Asn Pro Asp Ser Gly Val Asp Thr Lys Leu Leu Val Gly Pro Lys
            500                 505                 510

Lys Glu Arg Leu Asp Ile Lys Ala Ala Leu Ser Asn Ser Phe Gly Phe
    515                 520                 525

Gly Gly His Asn Ser Ser Ile Ile Phe Ala Pro Tyr Lys
    530                 535                 540

<210> SEQ ID NO 25
<211> LENGTH: 488
<212> TYPE: PRT
<213> ORGANISM: Glycine max
<220> FEATURE:
<223> OTHER INFORMATION: soybean (Gm) cultivar century
      beta-ketoacyl-acyl carrier protein (ACP) synthase (KASII), plastid
      3-keto-acyl-ACP synthase II-A (KASII-A)

<400> SEQUENCE: 25

Met Ala Ser Thr Thr Ser Ser Leu Cys Thr Trp Leu Val Ala Ala
  1               5                  10                  15

Cys Met Ser Val Thr Cys His Ala Asp Arg Thr Lys Thr Pro His Ala
            20                  25                  30

Met Phe Arg Ser Ser Lys Lys Ser Arg Tyr Ser Gln Phe Asn Val Cys
        35                  40                  45

Arg Ser Thr His Ser Gly Lys Thr Met Ala Val Ala Leu Gln Pro Thr
 50                  55                  60

Gln Glu Ile Thr Thr Ile Lys Lys Pro Pro Thr Lys Gln Arg Arg Val
 65                  70                  75                  80

Val Val Thr Gly Leu Gly Val Val Thr Pro Leu Gly His Glu Pro Asp
                 85                  90                  95

Ile Phe Tyr Asn Asn Leu Leu Asp Gly Ala Ser Gly Ile Ser Glu Ile
                100                 105                 110

Glu Thr Phe Asp Cys Ala Glu Tyr Pro Thr Arg Ile Ala Gly Glu Ile
            115                 120                 125

Lys Ser Phe Ser Thr Asp Gly Trp Val Ala Pro Lys Leu Ser Lys Arg
    130                 135                 140

Met Asp Lys Phe Met Leu Tyr Met Leu Thr Ala Gly Lys Lys Ala Leu
145                 150                 155                 160

Val Asp Gly Gly Ile Thr Asp Asp Val Met Asp Glu Leu Asn Lys Glu
                165                 170                 175
```

```
Lys Cys Gly Val Leu Ile Gly Ser Ala Met Gly Met Lys Val Phe
            180                 185                 190

Asn Asp Ala Ile Glu Ala Leu Arg Ile Ser Tyr Lys Lys Met Asn Pro
                195                 200                 205

Phe Cys Val Pro Phe Ala Thr Thr Asn Met Gly Ser Ala Met Leu Ala
    210                 215                 220

Met Asp Leu Gly Trp Met Gly Pro Asn Tyr Ser Ile Ser Thr Ala Cys
225                 230                 235                 240

Ala Thr Ser Asn Phe Cys Ile Leu Asn Ala Ala Asn His Ile Ile Arg
                245                 250                 255

Gly Glu Ala Asp Val Met Leu Cys Gly Gly Ser Asp Ala Ala Ile Ile
            260                 265                 270

Pro Ile Gly Leu Gly Gly Phe Val Ala Cys Arg Ala Leu Ser Gln Arg
        275                 280                 285

Asn Thr Asp Pro Thr Lys Ala Ser Arg Pro Trp Asp Ile Asn Arg Asp
        290                 295                 300

Gly Phe Val Met Gly Glu Gly Ala Gly Val Leu Leu Leu Glu Glu Leu
305                 310                 315                 320

Glu His Ala Lys Glu Arg Gly Ala Thr Ile Tyr Ala Glu Phe Leu Gly
                325                 330                 335

Gly Ser Phe Thr Cys Asp Ala Tyr His Val Thr Glu Pro Arg Pro Asp
            340                 345                 350

Gly Ala Gly Val Ile Leu Cys Ile Glu Lys Ala Leu Ala Gln Ser Gly
        355                 360                 365

Val Ser Lys Glu Asp Val Asn Tyr Ile Asn Ala His Ala Thr Ser Thr
        370                 375                 380

Pro Ala Gly Asp Leu Lys Glu Tyr Gln Ala Leu Met His Cys Phe Gly
385                 390                 395                 400

Gln Asn Pro Glu Leu Arg Val Asn Ser Thr Lys Ser Met Ile Gly His
                405                 410                 415

Leu Leu Gly Ala Ala Gly Gly Val Glu Ala Val Ala Thr Ile Gln Ala
            420                 425                 430

Ile Arg Thr Gly Trp Val His Pro Asn Ile Asn Leu Glu Asn Pro Asp
        435                 440                 445

Asn Gly Val Asp Ala Lys Val Leu Val Gly Ser Lys Lys Glu Arg Leu
        450                 455                 460

Asp Val Lys Ala Ala Leu Ser Asn Ser Phe Gly Phe Gly Gly His Asn
465                 470                 475                 480

Ser Ser Ile Ile Phe Ala Pro Tyr
                485

<210> SEQ ID NO 26
<211> LENGTH: 496
<212> TYPE: PRT
<213> ORGANISM: Zea mays
<220> FEATURE:
<223> OTHER INFORMATION: corn (maize, Zm) clone 1378666
      beta-ketoacyl-acyl carrier protein (ACP) synthase (KASII),
      3-oxoacyl-synthase I

<400> SEQUENCE: 26

Met Ala Ala Val Ala Gly Pro Leu Cys Thr Trp Leu Val Ala Ala Cys
  1               5                  10                  15

Leu Ser Ala Ala Cys Asp Ala Glu Glu Tyr Lys His Lys His Cys Cys
            20                  25                  30

Pro Gly Gly Ser Gly Ala Gly Gly Gly Val Met Leu Gly Gln Arg Arg
```

```
                35                  40                  45
Arg Leu Gly Ala Arg Arg Gly Leu Ala Arg Ser Gly Met Ala Met
 50                  55                  60
Ala Val Ala Leu Gln Ala Glu Arg Ser Val Ile Glu Lys Lys Pro
65                  70                  75                  80
Asp Ile Lys Gln Arg Arg Val Val Val Thr Gly Met Gly Val Thr
                85                  90                  95
Pro Leu Gly His Asp Pro Asp Val Phe Tyr Asn Asn Leu Leu Asp Gly
                100                 105                 110
Val Ser Gly Ile Ser Glu Ile Glu Arg Phe Asp Cys Ser Asn Phe Pro
                115                 120                 125
Thr Arg Ile Ala Gly Glu Ile Lys Ser Phe Ser Thr Asp Gly Trp Val
                130                 135                 140
Val Pro Lys Leu Ala Lys Arg Met Asp Lys Phe Met Leu Tyr Leu Ile
145                 150                 155                 160
Thr Ala Gly Lys Lys Ala Leu Glu Asn Gly Gly Leu Thr Glu Glu Leu
                165                 170                 175
Arg Asn Glu Leu Asp Lys Thr Arg Cys Gly Val Leu Ile Gly Ser Ala
                180                 185                 190
Met Gly Gly Met Lys Val Phe Asn Asp Ala Ile Glu Ala Leu Arg Val
                195                 200                 205
Ser Tyr Lys Lys Met Asn Pro Phe Cys Val Pro Phe Ala Thr Thr Asn
210                 215                 220
Met Gly Ser Ala Ile Leu Ala Met Asp Leu Gly Trp Met Gly Pro Asn
225                 230                 235                 240
Tyr Ser Ile Ser Thr Ala Cys Ala Thr Ser Asn Phe Cys Ile Leu Asn
                245                 250                 255
Ala Ala Asn His Ile Arg Arg Gly Glu Ala Asp Val Met Leu Cys Gly
                260                 265                 270
Gly Ser Asp Ala Pro Leu Ile Pro Ile Gly Leu Gly Gly Phe Val Ala
                275                 280                 285
Cys Arg Ala Leu Ser Gln Arg Asn Ser Asp Pro Thr Lys Ala Ser Arg
290                 295                 300
Pro Trp Asp Met Gly Arg Asp Gly Phe Val Met Gly Glu Gly Ala Gly
305                 310                 315                 320
Val Leu Val Leu Glu Glu Leu Glu His Ala Lys Glu Arg Gly Ala Thr
                325                 330                 335
Ile Tyr Ala Glu Phe Leu Gly Gly Ser Phe Thr Cys Asp Ala Tyr His
                340                 345                 350
Met Thr Glu Pro His Pro Glu Gly Arg Gly Ile Thr Leu Cys Ile Glu
                355                 360                 365
Lys Ala Leu Ala Asp Ala Gly Val Ala Arg Glu Ile Asn Tyr Val
                370                 375                 380
Asn Ala His Ala Thr Ser Thr Gln Ala Gly Asp Leu Lys Glu Tyr Glu
385                 390                 395                 400
Ala Ile Val Arg Cys Phe Arg Gln Asn Pro Gln Leu Arg Val Asn Ser
                405                 410                 415
Thr Lys Ser Met Thr Gly His Leu Ile Gly Ala Ala Gly Gly Ile Glu
                420                 425                 430
Ala Val Ala Ser Ile Gln Ala Ile Arg Thr Gly Trp Val His Pro Asn
                435                 440                 445
Leu Asn Leu Glu Asn Pro Glu Asp Thr Val Asp Val Gly Ile Leu Val
450                 455                 460
```

```
Gly Ser Gln Lys Glu Arg Cys Glu Val Lys Val Ala Leu Ser Asn Ser
465                 470                 475                 480

Phe Gly Phe Gly Gly His Asn Ser Ser Ile Leu Phe Ala Pro Phe Lys
                485                 490                 495
```

β-KETOACYL ACP-SYNTHASE II (KASII) GENE FROM *JESSENIA BATAUA*

CLAIM OF PRIORITY

This is a utility application and claims priority to Malaysian Patent Application No. PI 2011002288 titled "β-KETOACYL ACP-SYNTHASE II (KASII) GENE FROM *JESSENIA BATAUA*" filed on 23 May 2011.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 94370-889758.TXT, created on Oct. 1, 2013, 40,960 bytes, machine format IBM-PC, MS-Windows operating system, is hereby incorporated by reference in its entirety for all purposes.

FIELD OF TECHNOLOGY

The present invention relates to the field of plant genetic engineering, more particularly relates to the use of an isolated nucleic acid fragment from *Jessenia bataua*, which encodes a β-ketoacyl-ACP synthase (II) gene to modify the fatty acid composition in oil crops.

BACKGROUND

With the advent of biotechnology nowadays, rather than conventional plant breeding approaches, genetically modifying a crop trait to enhance the agricultural productivity as well as to meet the increasing demands for the industry is possible. For example, oil bearing plants could be genetically modified through the expression of incorporated foreign genes in their genome, thereby manipulating the fatty acid composition thereof for nutritional or functional purposes. Studies showed that the β-ketoacyl-ACP (acyl carrier protein) family of synthase enzymes (or also referred to as KAS) play a critical role in the fatty acid elongation system. The KAS enzyme catalyzes formation of carbon-carbon bonds by condensing a variety acyl chain precursors, which are generally the malonyl or methyl malonyl moieties from malonyl-ACP. There are four KAS enzymes: KASI, KASII, KASIII and KAS IV. KASII catalyzes the condensation of C18:0 with substrates C14-C16 acyl-ACP. It is, therefore, suggested that an increased in C18: chain fatty acids in plant oils could be observed by expressing in a transgenic plant the gene encoding the KAS II protein.

Accordingly, increasing attempts in isolating nucleic acid fragments encoding KAS protein, from either plants or microorganisms, have been known for oil crop's genetic engineering. For instance, US2004132189 (A1) describes a method of transforming a plant with a DNA sequence encoding β-ketoacyl-ACP synthase (KAS), which is derived from cynobacterial sources, and improves the oil quality of crops, especially soybean. Transgenic soybean seed based on this genetic modification method have a total saturated fatty acid of less than 3.5% compared to that of the wild type.

Another prior art document, U.S. Pat. No. 5,500,361 also describes the use of a β-ketoacyl-ACP synthase II gene isolated from soybean seed, to control the amount ratio of palmitic acid and stearic acid in oil-producing crops. Besides that, as disclosed in prior art document U.S. Pat. No. 6,348,642 (B1), a nucleic acid fragment encoding β-ketoacyl-ACP synthase derived from *Ricinus communis*, was incorporated into a host genome in an anti-sense orientation, and has shown to improve the lipid profile of the transgenic plant.

Since the KAS II protein shows a promise in the areas of plant oil modification, therefore, it is the primary object of the present invention to isolate a nucleic acid fragment encoding β-ketoacyl-ACP synthase II (KASII) from *Jessenia bataua*, which is rich in oleic acid content and has a low concentration of saturated fatty acid.

It is yet another object of the present invention to provide a recombinant DNA construct having a nucleic acid fragment encoding *Jessenia* β-ketoacyl-ACP synthase II (KASII) to transform oil crops, and thereby manipulating lipid profile thereof.

SUMMARY

The present invention relates to the use of an isolated nucleic acid fragment encoding β-ketoacyl ACP-Synthase (II) (KASII) derived from *Jessenia bataua* for manipulating the fatty acid composition in plants, particularly oil crops. Understandably, by transforming plants with a recombinant DNA construct that have said fatty acid synthase gene incorporated therein, the fatty acid composition of said transgenic plants, particularly levels of very long chain fatty acids could be enhanced.

One aspect of the present invention involves cloning *Jessenia* β-ketoacyl ACP-synthase (II) gene (JbKASII) into a p35S vector and subsequently transforming said construct into *Arabidopsis* plant cells for analyzing the biological function of the KASII protein. The expression of this recombinant DNA construct results in production of altered levels of fatty acid compositions in the transformed cells. However, it is observed that there is an elevated level of very long chain fatty acids, particularly arachidic acid (C20:0) and erucic acid (C22:1) but not stearic acid (C18:0) and oleic acid (C18:1), as expected. This finding implies that the JbKASII may have different substrate specificities from other KASII homologs of other species, although they share a significant similarity of amino acid sequence to one another.

BRIEF DESCRIPTION OF THE DRAWINGS

Example embodiments are illustrated by way of example and not limitation in the figures of the accompanying drawings, in which like references indicate similar elements and in which: FIG. 1 is a ClustalW multiple sequence alignment of β-Ketoacyl ACP-Synthase II (KASII) protein encoding sequences from *Jessenia bataua* (SEQ ID No. 1 NO:1), *Elaeis oleifera* (Eo, Protein Accession No. ACQ41833; SEQ ID NO:22), *Elaeis guineensis* (Eg; SEQ ID NO:21), *Arabidopsis thaliana* (At, Protein Accession No. AAK69603; SEQ ID NO:24), *Glycine max* (Gm, Protein Accession No. AAW88763; SEQ ID NO:25), *Zea mays* (Zm, Protein Accession No. ACG25173; SEQ ID NO:26) and *Jatropha curcas* (Jc, Protein Accession No. ABJ90469; SEQ ID NO:22).

Figure 2:
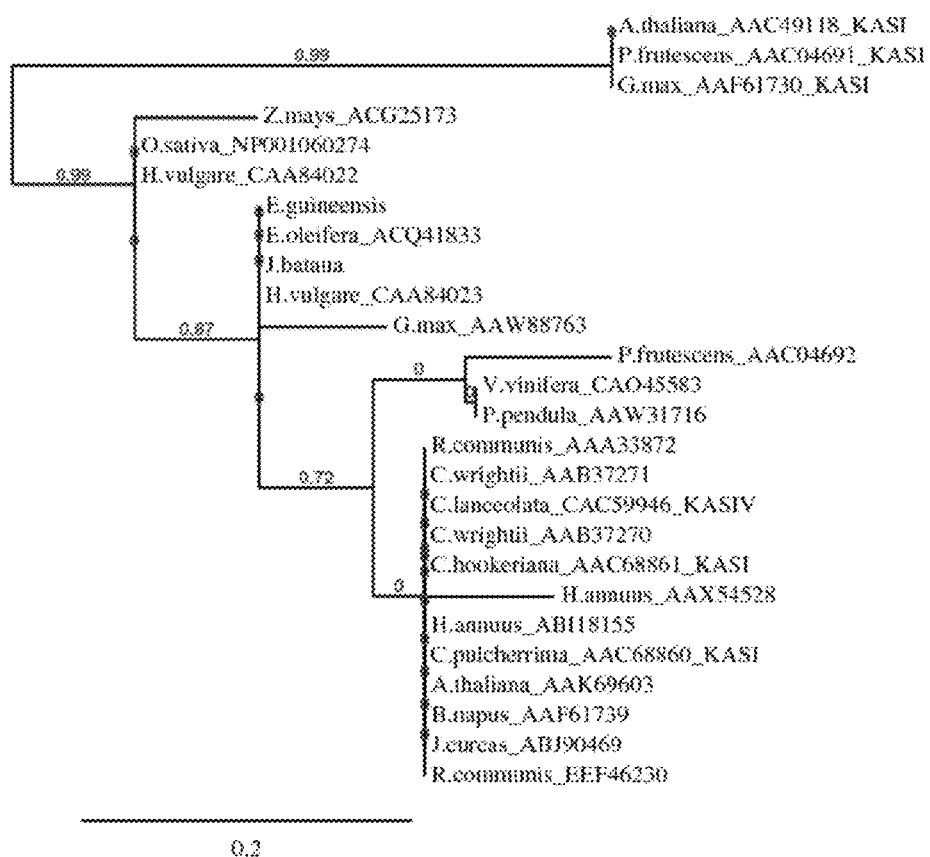
FIG. 2 is a phylogenetic tree of β-Ketoacyl ACP-Synthase (KAS) homologs from plants.

Other features of the present embodiments will be apparent from the accompanying drawings and from the detailed description that follows.

DETAILED DESCRIPTION

Further understanding of the object, construction, characteristics and functions of the invention, a detailed description with reference to the embodiments is given in the following.

The present invention describes an isolated nucleic acid fragment (SEQ ID NO:2) encoding β-ketoacyl ACP synthase II (KASII) from *Jessenia bataua*. Said nucleic acid fragment has an amino acid sequence represented by SEQ ID NO:1 in the Sequence Listing, which encodes an open reading frame that is closely related to KASII homologs from *Elaeis guineensis, Elaeis oleifera* and barley, based on protein sequence alignment and phylogenetic analysis.

However, in contrast to the β-ketoacyl ACP synthase (II) from these plant species, said *Jessenia* β-ketoacyl ACP synthase (II) does not catalyze elongation of palmitic acid (C16:0), but shares a substrate specificity with ketoacyl-CoA synthase (KCS) to elongate stearic acid (C18:0) and oleic acid (C18:1), forming arachidic acid (C20:0) and erucic acid (C22:1).

It is, therefore, by incorporating said nucleic acid fragment of the present invention or a part thereof in a desired organism, particularly oil crops, through any conventional transformation or transfection method, the fatty acid composition thereof could be modified. More suitably, very long chain fatty acids content of an oil crop, particularly the arachidic acid (C20:0) and erucic acid (C22:1) could substantially be enhanced if a recombinant construct comprising said nucleic acid fragment is introduced therein for expression.

Furthermore, as apparent to one skilled in the art, the levels of very long chain fatty acids can be regulated by varying the expression level of the nucleic acid fragment of the present invention in the transgenic organism or by coordinating expression of other genes involved in the relevant biosynthesis pathway such as desaturases and acyltransferases.

Apart from being used for genetic engineering, the nucleic acid fragment of the present invention could be comprehended by a skilled artisan accordingly, to be used in genetic mapping and breeding programs since they are informative and reliable.

BEST MODE FOR CARRYING OUT THE INVENTION

The preparation of the present invention is described in detail by referring to the experimental examples. It should be understood that these experimental examples, while indicating preferred embodiments of the invention, are given by way of better elucidation only. A person skilled in the art can ascertain the essential characteristics and embodiments of this invention, therefore various changes may be provided to adapt to various usages and conditions.

Plant Material and Total RNA Extraction

In this experimental study, plant materials, for example mesocarps and spear leaves of *Jessenia bataua* were provided by Research Station-MPOB Kluang, to extract their genomic DNA and total RNA, respectively according to CTAB extraction method by Doyle & Doyle and Zhen & Yang.

About 45 ml of freshly prepared extraction buffer, which consists of approximately 2% CTAB, 2% PVP (molwt 40,000), 100 mM Tris-HCl with pH8, approximately 25 mM EDTA, approximately 2M NaCl, approximately 0.05% spermidinetrihydrochloride, approximately β-mercaptoethanol (added before use), Chloroform-isoamylalcohol (24:1), approximately 10M LiCl was pre-warmed in a water bath at about 65° C.

Frozen powder of *Jessenia* mesocarp tissues in liquid nitrogen was transferred to the pre-warmed extraction buffer and was mixed homogenously followed by incubation at a temperature of roughly 65° C. for about 10 minutes. Thereafter, an equal volume of chloroform-isoamylalcohol was added to the mixture and vigorously shaken by centrifugation at approximately 10,000 g for about 10 minutes at nearly 4° C. Supernatant extracted was subsequently transferred to a new tube and re-extracted using chloroform-isomylalcohol through centrifugation as mentioned earlier.

Supernatant extracted from the second extraction step was spun at approximately 30,000 g for about 20 minutes at roughly 4° C., to pellet down and discard insoluble materials thereof. The supernatant was then treated with approximately 0.25 volumes of 10M LiCl, and stored at 4° C. overnight. The RNA was allowed to sediment, forming RNA pellet with centrifugation at 30,000 g for 30 minutes at 4° C. The resulted pellet was subjected to a washing step with 75% ethanol and followed by air-drying step for about 10 minutes prior to being dissolved in DEPC-treated water for storage at approximately −80° C. Centrifugation at 10,000 g for 5 minutes at about 4° C. should be performed if a cloudy suspension is formed in the DEPC-treated water.

Prior to being subjected to molecular applications such as RT-PCR, cDNA library construction, agarose gel electrophoresis and gene expression profiling, the purity of the resultant RNA pellet was estimated from A260/280 and A260/230 absorbency ratios. In one embodiment of the present invention, total mRNA transcripts from the purified RNA were obtained based on RT-PCR protocol provided by manufacturer of Gene Racer™ kit (Invitrogen™, US). Efficiency of RT reactions was then determined by amplifying GADPH (glyceraldehyde-3-phosphate dehydrogenase) transcript from cDNA.

Isolation of Full Length cDNA Sequence of JbKASII

*Jessenia* mesocarp total RNA as obtained from the previously described protocol was used to synthesis RACE-ready cDNA based on the GeneRacer™ (Invitrogen, US) user manual. According to this manual, total RNA was dephosphorylated, decapped, and ligated with GeneRacer RNA Oligo prior to being subjected to a reverse transcription (RT) process.

Eppendorf tubes containing RT reaction mixture of 1 μl GeneRacer™ Oligo dT primer (represented by SEQ ID NO:3 in the Sequence Listing), 10 μl of ligated RNA, 2 μl dNTP mix (25 mM), 4 μl of 5× reaction buffer, 1 μl of 0.1 mM DTT, 1 μl of RNaseOUT™ (40 U/μ1) and 1 μl of Thermoscript™ RT (150/μl) were subjected to a T Profesional thermal cycler (Biometra™, Germany) at 55[deg.] C. for 60 minutes for amplification. This PCR reaction was terminated by 5 minute-incubation at 85° C. followed by introduction of approximately 1 μl (2 U) of *E. coli* RNase H. The mixture was subsequently incubated at approximately 37° C. for 20 minutes.

Four primers as shown in Table 1 and represented by SEQ ID No 4, 5, 6, 7 in the Sequence Listing were designed to amplify either 3' or 5' cDNA ends of the KASII genes. These primers were based on plants KASII conserved domains. It should be understood that the primary primer GSP 1 and the nested primer GSP2 were used to obtain JbKASII cDNA partial 3' fragments from 3'RACE PCR, whereas the partial 5' fragments were amplified when GSP 3 and GSP 4 were used during the 5'RACE PCR.

TABLE 1

| Primers for 3' RACE and 5'RACE PCR | | SEQ ID NO: |
|---|---|---|
| Primers | Sequence | |
| GSP 1 | 5'GCCACATCTGAAGGTAGAG 3' | 4 |
| GSP 2 | 5'TGAGTTATGCCCACCGCCTC 3' | 5 |
| GSP 3 | 5'CACCAGATGGTGTTGAAGTTGCATGAGC 3' | 6 |
| GSP 4 | 5'CCTGATTCTGCTAGCGCCTTCTCAATGC 3' | 7 |

Amplified RACE-PCR products, for example, 3' end fragment sequence of approximately 1 kb and 5' end fragment sequence of approximately 600 bp were generated based on the method as described above. These fragments also showed approximately 75% sequence identical to that of *Elaeis guineensis* (oil palm) KASII. In order to obtain a full-length JbKASII cDNA sequence, these 3' end- and 5' end fragments by any conventional end-to-end PCR protocol in the art. However, having considered the nucleotide sequences of the 5'- and the 3'-RACE products, gene-specific primers, namely gKASF4, represented by SEQ ID No. 12 in the Sequence Listing, or gKASF6, represented by SEQ ID No. 13 in the Sequence Listing, were designed and used together with a reverse primer gKASR6, represented by SEQ ID No. 14 in the Sequence Listing, in this reaction.

A single PCR product of approximately 2 kb was resulted from the end-to-end PCR based on primer combinations of gKASF4-gKASR6 and gKASF6-gKASR6. The putative JbKASII cDNA was 1874 in length; it found to share high sequence similarity to other palm species such as *E. guineensis*. By using ORF Finder Software, it was observed that this JbKASII cDNA has an open reading frame (ORF) starts at A229TG or the 77$^{th}$ codon and ends at T1693AG or the 565th codon. Understandably, this JbKASII cDNA encodes for a 488 amino acid polypeptide, with 228 base pairs and 179 base pairs of 5'- and 3' untranslated region, respectively. Furthermore, it was also predicted that this full length JbKASII cDNA, preferably by an online-based prediction tool Compute pi/Mw, has a pi of approximately 7.08 and a molecular mass of approximately 52 kDa.

Based on in silico analysis, it was observed that JbKASII shows a significant similarity to KASII proteins isolated from various monocots and dicots. The amino acid sequence of the JbKASII shared a significant sequence identity to KASII homologs from plants, for example, *Elaeis guineensis* (97.5% identity), *Jatropha curcas* (79.5% identity), *Arabidopsis thaliana* (77% identity), soybean (84.4% identity) and rice (83.7% identity).

Figure 1:
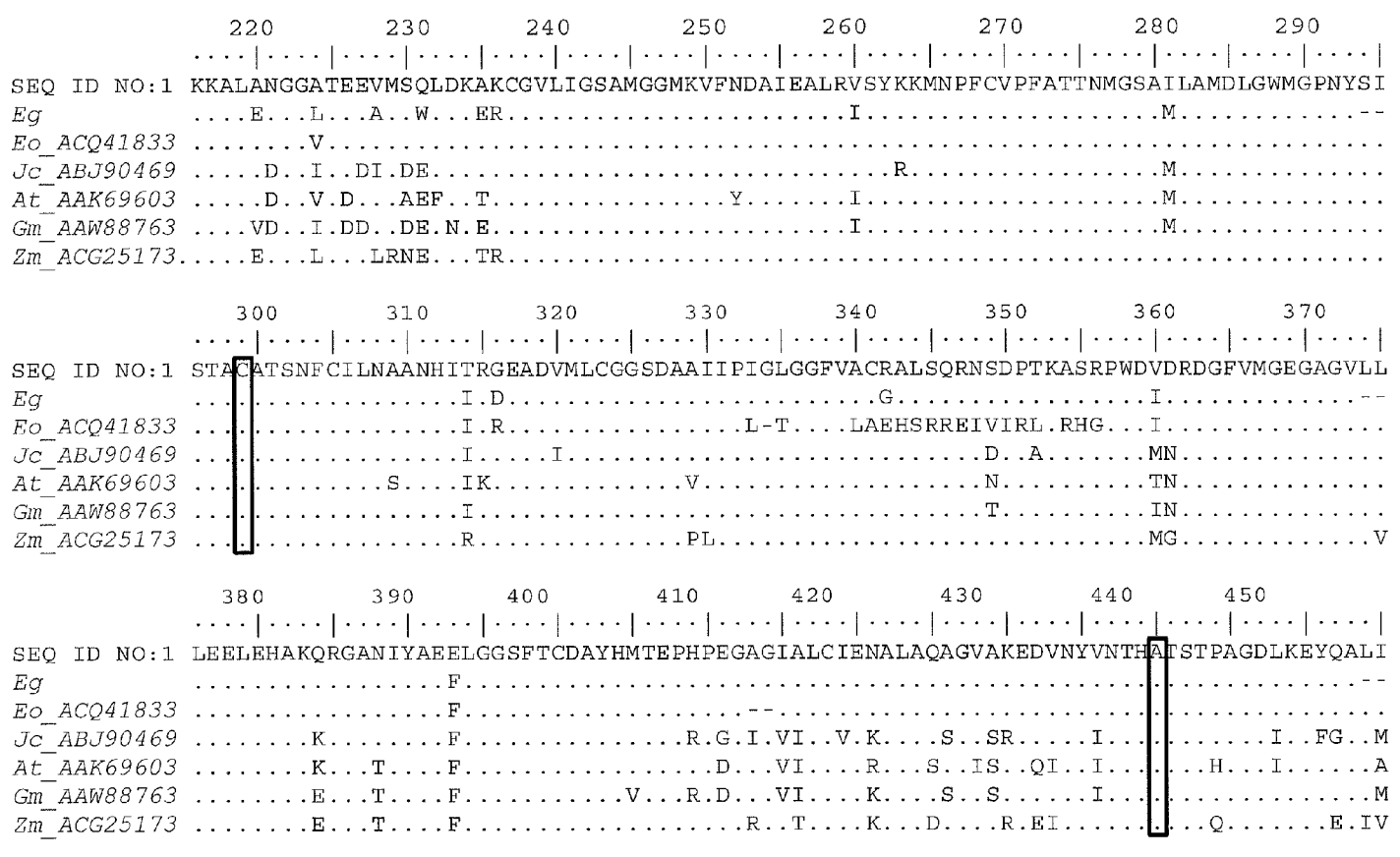

FIG. 1 shows the ClustalW multiple sequence alignment of the amino acid sequence of JbKASII with KASII from *Elaeis guineensis, Elaeis oleifera* (Eo, Protein Accession No. ACQ41833), *Arabidopsis thaliana* (At, Protein Accession No. AAK69603), *Glycine max* (Gm, Protein Accession No. AAW88763), *Zea mays* (Zm, Protein Accession No. ACG25173) and *Jatrophacurcas* (Protein Accession No. ABJ90469). The amino sequence of JbKASII designated as SEQ ID NO. 1, as depicted in FIG. 1, is highly similar to that of the KASII homologs from other plants. Like other KASII homologs, JbKASII has a highly conversed active site triad motif, Cys299-His439-His 475 (in rectangular boxes as shown in FIG. 1). Two protein domains, namely N-terminal KASII domain and C-terminal KASII domain were found in the JbKASII amino acid sequence. Protein structure analysis suggested that enzymatic activity of the JbKASII proteins lies within these two protein domains. However, in contrast to most plant KASII homologs, JbKASII protein does not have a plastid targeting signal.

Referring to the phylogenetic tree of KAS homologs from various plant species, as depicted in FIG. 2, JbKASII protein is most related to KAS homologs from *E. oleifera* and *E. guineensis*. KASII homologs of *O. sativa, Z. mays*, and *H. vulgareare* diverged to form an independent branch of the phylogram, although they share the same ancestor with that of the *Jessenia bataua*. It, therefore, suggested that these sister groups may have different enzymatic efficiencies or substrate specificities. An out-group, which branches off at the base of the phylogeny and comprises of KAS homologs from *A. thaliana, P. frutescens* and *G. max* had also suggested that this clade may be consisted of KASI protein, but not KASII protein.

Southern Blot Analysis

In one embodiment, three probes were employed to examine the genomic organization of JbKASII in *Jessenia* genome. These probes include KASII domain-specific probes that recognize sequences in the N-terminus and C-terminus to determine the number of JbKASII paralogs in the *Jessenia* genome and a 3'UTR-specific probe of approximately 200 bp in length for detecting the gene copy number of JbKASII.

KASII domain-specific probes for the C-terminus was amplified from the JbKASII cDNA clone using primers JkasCF, represented by SEQ ID No. 15 in the Sequence Listing, and JkasCR, represented by SEQ ID No. 16 in the Sequence Listing, whereas primers such as JkasNF, represented by SEQ ID No. 17 in the Sequence Listing, and JkasNR, represented by SEQ ID No. 18 in the Sequence Listing, were used to synthesis KASII domain-specific probe for the N-terminus. For the 3'UTR-specific probe synthesis, primers JK3UTRF, represented by SEQ ID No. 19 in the Sequence Listing, and JK3UTRR, represented by SEQ ID No. 20 in the Sequence Listing, were used.

The southern blot analysis of the present invention was carried out according to Sambrook et. al. *Jessenia* genomic DNA was digested with DraI, EcoRV, HindIII, PvuII, StuI and XhoI (New England Biolabs USA) and resolved on a 0.8% agarose gel and subsequently being transferred to Nylon membranes (DuPont, USA). It was noted that these well-prepared probes were radio-labelled with 32P dCTP according to the Prime-It II Random Primer labeling Kit (Straragene, USA) user manual and hybridized overnight at 65° C., followed by 1× high-stringency wash.

Figure 3:
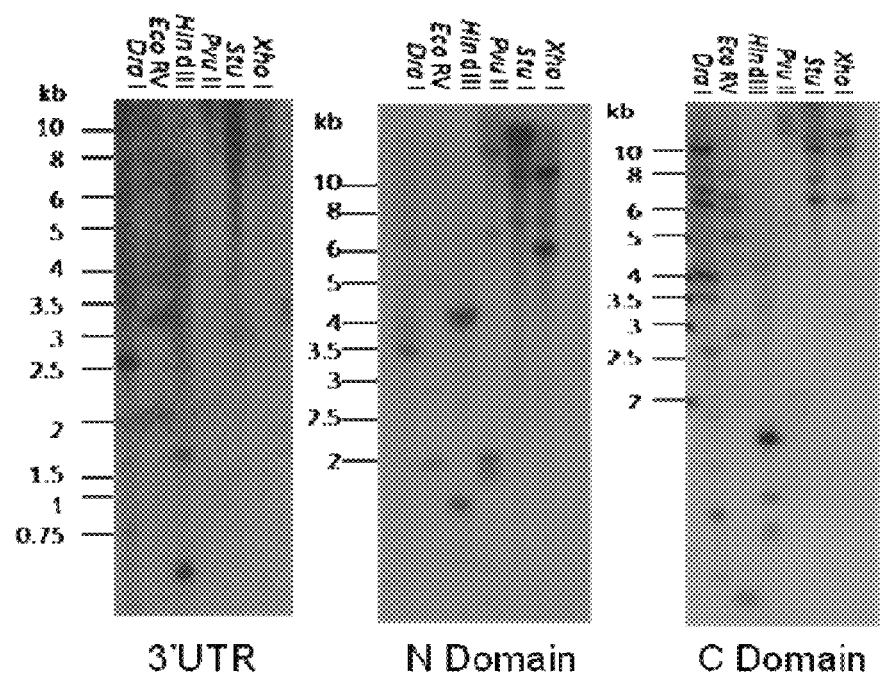
FIG. 3 shows the result of the Southern blot analysis of JbKASII embodying the present invention.

Based on the Southern Blot analysis protocol as mentioned above, it was observed that, in FIG. 3, the JbKASII of the present invention is a single copy gene as only a single 2.75 kb band, and was detected in the DraI-digested DNA pool. Multiple bands were detected from the five DNA libraries generated using the restriction enzymes, namely DraI, EcoRV, HindIII, PvuII, StuI and XhoI, by the domain-specific probes. It, therefore, showed that rather than the KASII gene sequence, similar N-terminus and C-terminus KASII domains may also be found in other gene sequences of the *Jessenia* genome. It also suggested that, there are many paralogs in the *Jessenia* genome although it is a single copy gene that does not undergo gene duplication.

Expression of *Jessenia bataua* KASII (JbKASII) in *E. coli*

For gaining a better understanding of the biological function of the isolated JbKAS sequence, a His-tagged cDNA fusion of JbKASII was constructed and designated as pET32a: His-JbKASII-His. This pET32a:His JbKASII-His was generated when a putative 1467 by ORF of JbKASII was amplified and cloned into a linearized pET-32a (+) vector (Novagen). Primers BamHI-KasF, represented by SEQ ID No 8 in the Sequence Listings, and Not1-KasR, represented by SEQ ID No. 9 in the Sequence Listings, were employed to amplify the ORF. The expression cassette based on the ORF of JbKASII and the pET-32a (+) vector was subsequently transformed expressed by six different *E. coli* strains, preferably the BL21, BL21 (DE3), BL21 (DE3) pLysS, Rosetta-gami, Rosetta-gami B (DE3) pLysS and Origami (DE3). The preferred transformation was heat shock transformation.

Figure 4:
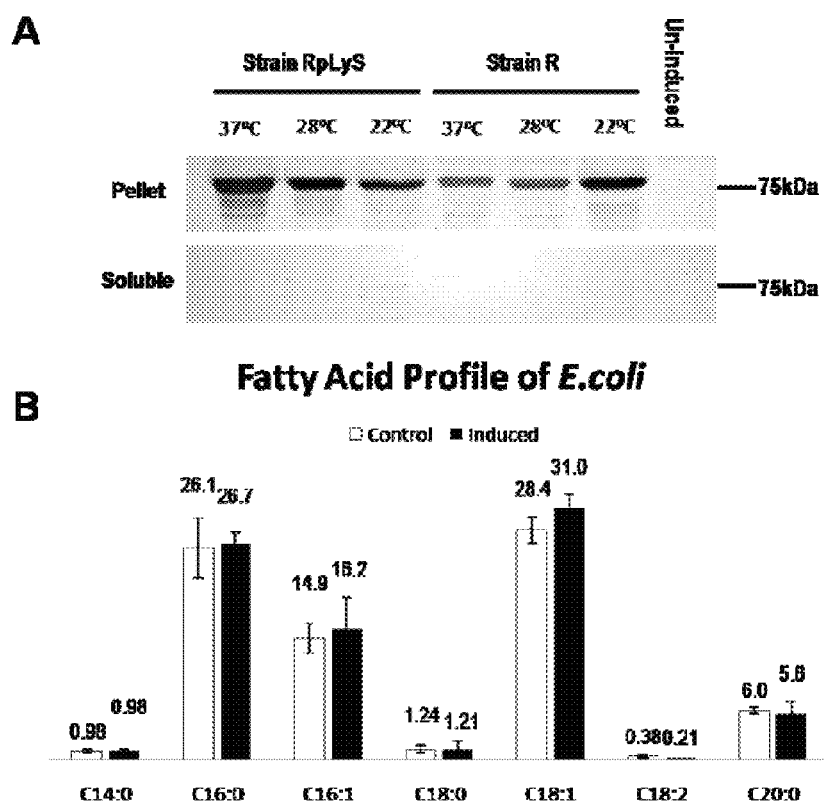
FIG. 4A shows the JbKASII solubility when being expressed in *E. coli* at approximately
FIG. 4B is a fatty acid profile of *E. coli* cultures over-expressing JbKASII, particularly the strain Rosetta-gami B (DE3)pLysS incubated at approximately 22° C.

Proteins were extracted from the recombinants JbKASII expressed in *E. coli* cultures, particularly strains BL21, BL21 (DE3), BL21(DE3)pLysS, Rosetta-gami B(DE3)pLysS (RpLyS), Origami (DE3) and Rosetta-gami (R) that had been incubated at 37° C., 28° C., and 22° C., respectively and followed by SDS-PAGE analysis to determine solubility thereof. Similar to most bacterial cell factories, recombinant proteins expressed in the *E. coli* cultures, particularly the only the Rosetta-gami B (DE3)pLysS and Rosetta-gami strains had failed to fold property and accumulated a copious amount of insoluble recombinants JbKASII at 37° C., as shown in FIG. 4A. These insoluble recombinant proteins, as understood by one skilled in the art, are non-functional inclusion bodies.

In addition, the fatty acid profile of *E. coli* cultures over-expressing JbKASII particularly the strain of Rosetta-gami B (DE3)pLysS incubated at about 22° C., as shown in FIG. 4*b*, had further supported that the misfolded proteins in the *E. coli* cultures over-expressing JbKASII is dysfunctional and are enzymatically inactive. The fatty acid composition of *E. coli* cultures over-expressing JbKASII was not significantly different from that of the un-induced control cultures. This observation could be explained that the lack of condensing activity of recombinant JbKASII or an overproduction of JbKASII in the *E. coli* cultures may inhibit fatty acid synthesis.

Expression of *Jessenia bataua* KASII (JbKASII) in *Arabidopsis thaliana*

Inconclusive results from the expression study of recombinant JbKASII in *E. coli* due to the inclusion bodies formation, as described previously, had encouraged the present inventors to express the JbKASII cDNA fusion constructs in *Arabidopsis thaliana*.

Two JbKASII Green Fluorescent Protein (GFP) fusion constructs were generated using Gateway recombination cloning technology (Invitrogen, US) for this expression study. These JbKASII GFP fusion constructs included p35S:GFP-JbKASII and p35S:JbKASII-GFP, which were characterized that having a GFP tagged to the C-terminal and N-terminal of the JbKASII protein, respectively.

In order to generate the N-terminal GFP fusion, approximately 1.5 kb cDNA of JbKASII was cloned as an attB1-JbKASII-stop-attB2 fragment into pDNOR211 to form pDNOR207-JbKASII-stop. The clone was subsequently sequenced and sub-cloned into the destination vector, p35S, to generate p35S:JbKASII-GFP. On the other hand, the p35S:GFP-JbKASII fusion constructs was preferably synthesis when the sequence pNOR207: JbKASII was sub-cloned into p35S vector. Both vectors were subjected to multiple restriction enzyme digestions to ensure that the insertion of the JbKASII cDNA was correctly oriented.

These well-prepared binary constructs were introduced into wild type *Arabidopsis*, particularly *Arabidopsis thaliana* (ecotype Columbia) based on *Agrobacterium*-mediated floral dipping method. The resultant transformants, which had a single locus insertion were subsequently selected and propagated to T3 generation, where seeds obtained therefrom were subjected to fatty acid analysis.

Prior to being subjected to a fatty acid analysis process, genotype of transgenic plant from generated from the T3 generation, which are either harboured the GFP-JbKASII transgene (C1) or the JbKASII-GFP transgene (C2) were determined by GFP-specific primers, preferably BamHI-GFP6-F, represented by SEQ ID No. 10 in the Sequence Listing, and EcoRI-GFP6-R, represented by SEQ ID No. 11 in the Sequence Listing, on a hydromycin-containing (15 μg/ml) MS medium.

Fatty acids were extracted from identified plants, particularly, seeds thereof, according to the following protocols: Approximately 0.1 g *Arabidopsis* seeds (about 5000 seeds) was initially incubated for roughly 1 hour at room temperature in about 7.5 ml extraction solvent consisting of water:(2%) HCl-acidified methanol:chloroform at a ratio of approximately 0.8:2:1. The suspension was spun down, and supernatant resulted therefrom was mixed with approximately 2.5 ml water and approximately 2.5 ml chloroform, to extract an organic fraction. The organic fraction was filtered using a silicone-treated IPS paper (Whatman, UK) to obtain fatty acids thereof.

The resultant fatty acids were then subjected to an esterification process, where approximately 2 ml toluene and approximately 2 ml 1% $H_2SO_4$-modified methanol were added to the fatty acids and allowed 2-hour incubation at 80° C. FAMEs were extracted by addition of 5% NaCl and 2 ml hexane to the esterified mixture, followed by collection of upper layer fraction after separation by centrifugation.

The FAMEs were concentrated under nitrogen gas streaming and re-constituted in approximately 0.5 ml hexane. The concentrated FAME samples were separated on a 30 m×0.25 mm DB WAX capillary column of a Perkin Elmer Clams 500 chromatograph. Preferably, fatty acid composition was expressed as relative means, which were calculated based on an external FAME standards mix, RM3 (Supelco, USA) run concurrently with each analysis.

Figure 5A:
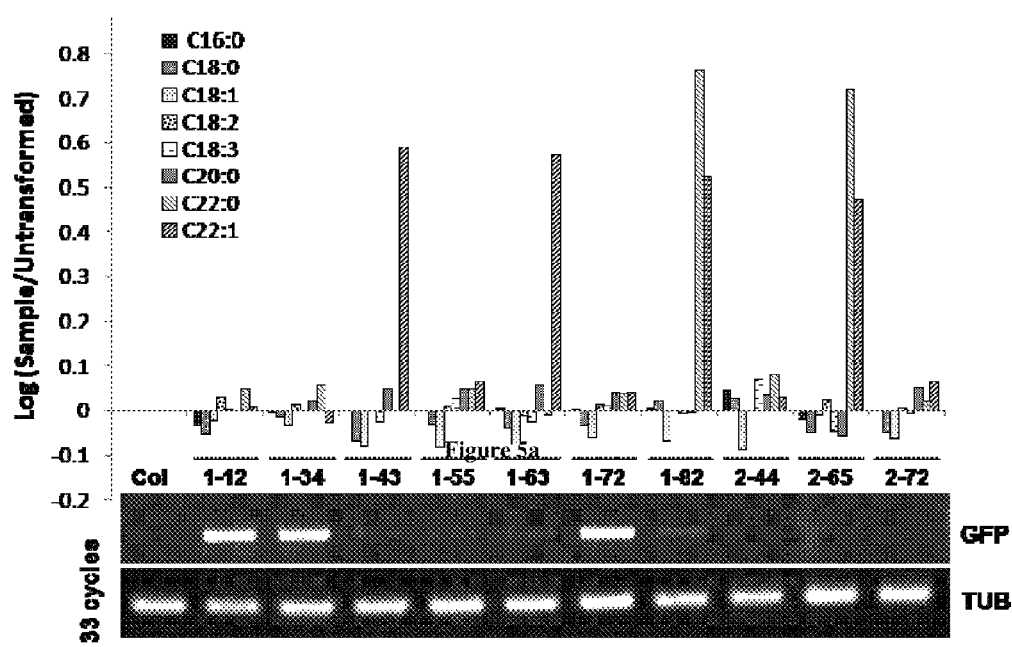
FIG. 5A shows a fatty acid profile and RT-PCR analysis of transgenic *Arabidopsis* plant expressing JbKASII (Col lines).

FIG. 5A is a fatty acid profile of mature transgenic *Arabidopsis* seeds from 10 independent T3 lines, of which 7 lines were transgenic plants harboured the GFP-JbKASII transgene (designated as C1) and another 3 lines were transgenic plants harboured the JbKASII-GFP transgene (designated as C2). It is noted that the relative fatty acid composition from each line was compared to that of the untransformed wild type *Arabidopsis*. In the other words, fatty acid profile of each line was based on the ratios of transgenic: untransformed fatty acids.

As KASII homologs from the plant kingdom are known to elongate palmitic acid (C16:0) to strearic acid (C18:0). However, as shown in FIG. 5A, an unexpectedly decreased of fatty acids, particularly the stearic acid (C18:1) (in all independent lines) and the oleic acid (C18:0) (8 lines out of 10) in the p35S-JbKASII transgenic seeds, was observed. Interestingly, such reduction of the fatty acids C18:0 and C18:1 was accompanied by approximately 1 to 3-fold increased of C22:1 (8 lines out of 10). Furthermore, in lines C1-82 and C2-65, a significant elevation in C22:0 of up to approximately 5-fold was also observed. This observation, therefore, suggested that the over-expression of JbKASII in *Arabidopsis* results in accumulation of fatty acid C22:0 and C22:1 with fatty acids C18:0 and C18:1 as the substrates for this fatty acid biosynthesis process.

However, because of the phenotype of these transgenic plants was not expressed uniformly, the GFP transgene expression level in each transgenic plant was then determined using semi-quantitative RT-PCR. In a preferred embodiment, the semi-quantitative RT-PCR was performed using Quanti-Tect RT kit (Qiagen, Germany) according to the manufacturer's instructions. Briefly, approximately 1 µg RNA was converted to first strand cDNA in a 20 µl reaction containing about 1 µl RT primer mix. A serial dilution of the cDNA samples was prepared and used in subsequent PCR reactions with the following cycle conditions: 95° C., 30 seconds; 65° C., 30 seconds; 72° C., 60 seconds for 33 cycles. Arabodopsis Tubulin gene was employed as the loading control.

It was notice that the transgenic lines with a pronounced increment of fatty acid C22:1 and C22:0, for example, the line C1-43, C1-63, C1-82 and C2-65 did not show a high abundance of GFT transcripts as those transgenic lines with weak fatty acid phenotype did, as shown in FIG. 5A. It implied that the accumulation of the very long chain fatty acids, particularly C22:1 and C22:0 in transgenic plants is inversely related to the JbKASII transgene expression levels. Two possibilities may account for this finding: either JbKASII transcription was silenced and therefore, weakened its condensing activities, or the elongating activities of the JbKASII were met with bottleneck due to a rate-limiting factor.

Previous studies showed that the lack of acyl-CoA substrates in the acyl-CoA pool has restricted elongated C20 fatty acid synthesis, and hence disrupts acyl-CoA-dependent elongation. This implies that proper channeling of the desaturated C18:0 and C18:1 into endoplasmic recticulumacyl-CoA pool is critical for VLCFA accumulation. Therefore, accumulation of VLCFA can be regulated not merely by varying expression levels of the JbKASII transgene; however, it can be achieved by coordinating expression of other genes involved in the relevant biosynthesis pathway, desaturases and acyltransferases, for example.

Although there was no significant increase of fatty acid, particularly the C18:0 in the p35S-JbKASII transgenic *Arabidopsis* seeds, however, the presence of KASII paralogs with conserved KAS domains in the *Jessenia* genome was believed that might lead to synthesis of VLCFA at the expense of fatty acids, C16:0. Accordingly, a functional complementation test to determine whether the JbKASII transgene complements with *Arabidopsis* KASII mutant, fatty acid biosynthesis 1 (fab1) was performed. Two fab1 mutants, namelyfab1-1 and fab1-2 were characterized for this complementation test. The fab1-1 is an EMS mutant with a L337F substitution in the active site of KASII while the fab1-2 is a T-DNA mutant with T-DNA insertion in the sixth introns of FAB1 locus. Both mutant genes showed deficiency in C16:0 condensing activities due to dysfunctional KASII enzymes. As a result, a high level of C16:0 accumulated in seeds and leaves would be observed.

Difficulties in germinating embryo lethal fab1-1 seeds had suggested to transform heterozygous FAB/fab1-2 with a single transgene insertion, either p35S: GFP-JbKASII or p35S:JbKASII-GFP, generating FAB1/fab1-2 transformants. These transformants were subsequently recovered by genotyping and propagated to T3 generation. Fatty acid profiling was performed on 6 independent homozygous transgenic lines from the T3 generation. These 6 independent lines included 5 lines harboured p35S: GFP-JbKASII (designated as F1) and 1 line harboured p35S: GFP-JbKASII-GFP (designated as F2).

Figure 5B:
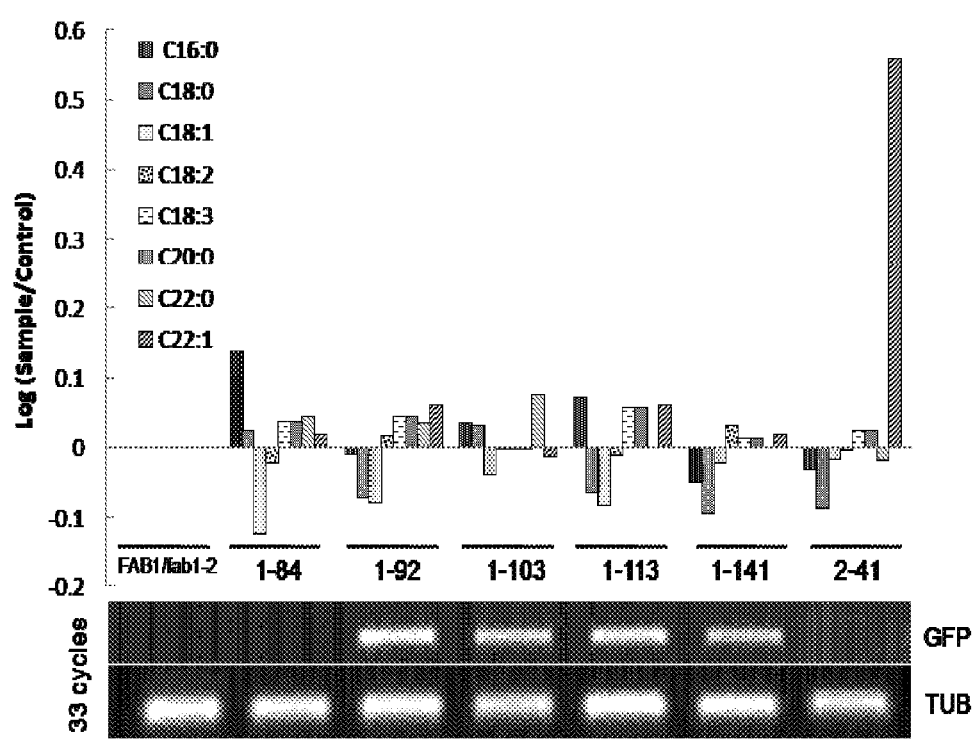
FIG. 5B shows a fatty acid profile and RT-PCR analysis of transgenic *Arabidopsis* plant expressing JbKASII (FAB1/fab1-2 lines).

As illustrated in FIG. 5B, there was no significant reduction of fatty acids, C18:0 and C18:1 observed in these independent homozygous JbKASII transgenic lines. However, these lines had shown an appreciation of C22:1. For example, the line F2-41 had approximately 3.6-fold increase of C22:1. Notably, this transgenic line, F2-41, had weak transgene expression of JbKASII, and the GPT transcripts could barely be detected. Furthermore, no consistent reduction in C16:0 was observed in the FAB1/fab1-2 plants complemented with JbKASII compared to that of the untransformed FAB1/fab1-2 plants. This could be explained that the fab1-2 may not functionally be complemented by the JbKASII.

To confirm that the fab1-2 is not complemented by JbKASII, up to 100 individuals segregating for FAB1/fab1-2 were genotyped. As the *Arabidopsis* KASII knock-out mutant, fab1-2 is an embryo lethal and segregates at a distorted 2 (FAB1): 1 (FAB/fab1-2) ratio. Therefore, complementation with wild-type copy of AtKASII could restore the 1 (FAB1):2(FAB1/fab1-2): 1(fab1-2) segregation. No homozygous fab1-2/fab1-2 plants were recovered from the genotyping, and thus confirming that the JbKASII does not complement with the fab1-2 or the JbKASII fails to rescue fab1-2. The previous hypothesis stated stating that the JbKASII might be involved in palmitic acid (C16:0) elongation was therefore rejected and it was confirmed that the JbKASII functionally resembles keto-acyl-CoA synthase (KCS). Both KSC and JbKASII share the same substrate specificity; they preferentially elongate stearic and oleic acid, but not palmitic acid.

Although the present invention has been described with reference to the preferred embodiments and examples thereof, it is apparent to those skilled in the art that a variety of modifications and changes may be made without departing from the scope of the present invention which is intended to be defined by the appended claims.

REPLACEMENT DETAILED DESCRIPTION

Further understanding of the object, construction, characteristics and functions of the invention, a detailed description with reference to the embodiments is given in the following.

The present invention describes an isolated nucleic acid fragment encoding β-ketoacyl ACP synthase II (KASII) from *Jessenia bataua*. Said nucleic acid fragment has an amino acid sequence represented by SEQ ID No. 1 in the Sequence Listing, which encodes an open reading frame that is closely related to KASII homologs from *Elaeis guineensis, Elaeis oleifera* and barley, based on protein sequence alignment and phylogenetic analysis.

However, in contrast to the β-ketoacyl ACP synthase (II) from these plant species, said *Jessenia* β-ketoacyl ACP synthase (II) does not catalyze elongation of palmitic acid (C16: 0), but shares a substrate specificity with ketoacyl-CoA synthase (KCS) to elongate stearic acid (C18:0) and oleic acid (C18:1), forming arachidic acid (C20:0) and erucic acid (C22:1).

It is, therefore, by incorporating said nucleic acid fragment of the present invention or a part thereof in a desired organism, particularly oil crops, through any conventional transformation or transfection method, fatty acid composition thereof could be modified. More suitably, the very long chain fatty acid acids content of an oil crop, particularly the arachidic acid (C20:0) and erucic acid (C22:1) could substantially be enhanced if a recombinant construct comprises of said nucleic acid fragment is introduced therein for expression.

Furthermore, as apparent to one skilled in the art, the levels of very long chain fatty acids can be regulated by varying expression level of the nucleic acid fragment of the present invention in the transgenic organism or by coordinating expression of other genes involved in the relevant biosynthesis pathway such as desaturases and acyltransferases.

Apart from being used for genetic engineering, the nucleic acid fragment of the present invention could be comprehended by a skilled artisan accordingly, to be used in genetic mapping and breeding programs since they are informative and reliable.

BEST MODE FOR CARRYING OUT THE INVENTION

The preparation of the present invention is described in detail by referring to the experimental examples. It should be understood that these experimental examples, while indicating preferred embodiments of the invention, are given by way better elucidation only. A person skilled in the art can ascertain the essential characteristics and embodiments of this invention, therefore various changes may be provided to adapt to various usages and conditions.

Plant Material and Total RNA Extraction

In this experimental study, plant materials, for example mesocarps and spear leaves of *Jessenia bataua* were provided by Research Station-MPOB Kluang, to extract their genomic DNA and total RNA, respectively according to CTAB extraction method by Doyle & Doyle and Zhen & Yang.

About 45 ml of freshly prepared extraction buffer, which consists of approximately 2% CTAB, 2% PVP (molwt 40,000), 100 mM Tris-HCl with pH8, approximately 25 mM EDTA, approximately 2M NaCl, approximately 0.05% spermidinetrihydrochloride, approximately β-mercaptoethanol (added before use), Chloroform-isoamylalcohol (24:1), approximately 10 M LiCl was pre-warmed in a water bath at about 65° C.

Frozen powder of *Jessenia* mesocarp tissues in liquid nitrogen was transferred to the pre-warmed extraction buffer and was mixed homogenously followed by incubation at a temperature of roughly 65° C. for about 10 minutes. Thereafter, an equal volume of chloroform-isoamylalcohol was added to the mixture and vigorously shaken by centrifugation at approximately 10,000 g for about 10 minutes at nearly 4° C. Supernatant extracted was subsequently transferred to a new tube and re-extracted using chloroform-isomylalcohol through centrifugation as mentioned earlier.

Supernatant extracted from the second extraction step was spun at approximately 30,000 g for about 20 minutes at roughly 4° C., to pellet down and discard insoluble materials thereof. The supernatant was then treated with approximately 0.25 volumes of 10M LiCl, and stored at 4° C. overnight. The RNA was allowed to sediment, forming RNA pellet with centrifugation at 30,000 g for 30 minutes at 4° C. The resulted pellet was subjected to a washing step with 75% ethanol and followed by air-drying step for about 10 minutes prior to being dissolved in DEPC-treated water for storage at approximately −80° C. Centrifugation at 10,000 g for 5 minutes at about 4° C. should be performed if a cloudy suspension is formed in the DEPC-treated water.

Prior to being subjected to molecular applications such as RT-PCR, cDNA library construction, agarose gel electrophoresis and gene expression profiling, the purity of the resultant RNA pellet was estimated from A260/280 and A260/230 absorbency ratios. In one embodiment of the present invention, total mRNA transcripts from the purified RNA were obtained based on RT-PCR protocol provided by manufacturer of Gene Racer™ kit (Invitrogen™, US). Efficiency of RT reactions was then determined by amplifying GADPH (glyceraldehyde-3-phosphate dehydrogenase) transcript from cDNA.

Isolation of Full Length cDNA Sequence of JbKASII

*Jessenia* mesocarp total RNA as obtained from the previously described protocol was used to synthesis RACE-ready cDNA based on the GeneRacer™ (Invitrogen, US) user manual. According to this manual, total RNA was dephosphorylated, decapped, and ligated with GeneRacer RNA Oligo prior to being subjected to a reverse transcription (RT) process.

Eppendorf tubes containing RT reaction mixture of 1 μl GeneRacer™ Oligo dT primer (represented by SEQ ID NO:3 in the Sequence Listing), 10 μl of ligated RNA, 2 μl dNTP mix (25 mM), 4 μl of 5× reaction buffer, 1 μl of 0.1 mM DTT, 1 μl of RNaseOUT™ (40 U/μl) and 1 μl of Thermoscript™ RT (150/μl) were subjected to a T Profesional thermal cycler (Biometra™, Germany) at 55[deg.] C. for 60 minutes for amplification. This PCR reaction was terminated by 5 minute-incubation at 85° C. followed by introduction of approximately 1 μl (2 U) of *E. coli* RNase H. The mixture was subsequently incubated at approximately 37° C. for 20 minutes.

Four primers as shown in Table 1 and represented by SEQ ID No 4, 5, 6, 7 in the Sequence Listing were designed to amplify either 3' or 5' cDNA ends of the KASII genes. These primers were based on plants KASII conserved domains. It should be understood that the primary primer GSP 1 and the nested primer GSP2 were used to obtain JbKASII cDNA partial 3' fragments from 3' RACE PCR, whereas the partial 5' fragments were amplified when GSP 3 and GSP 4 were used during the 5' RACE PCR.

TABLE 1

Primers for 3' RACE and 5'RACE PCR

| Primers | Sequence |
| --- | --- |
| GSP 1 | 5'GCCACATCTGAAGGTAGAG 3' |
| GSP 2 | 5'TGAGTTATGCCCACCGCCTC 3' |
| GSP 3 | 5'CACCAGATGGTGTTGAAGTTGCATGAGC 3' |
| GSP 4 | 5'CCTGATTCTGCTAGCGCCTTCTCAATGC 3' |

Amplified RACE-PCR products, for example, 3' end fragment sequence of approximately 1 kb and 5' end fragment sequence of approximately 600 bp were generated based on the method as described above. These fragments also showed approximately 75% sequence identical to that of *Elaeis guineensis* (oil palm) KASII. In order to obtain a full-length JbKASII cDNA sequence, these 3' end- and 5' end fragments by any conventional end-to-end PCR protocol in the art. However, having considered the nucleotide sequences of the 5'- and the 3'-RACE products, gene-specific primers, namely gKASF4, represented by SEQ ID No 12 in the Sequence Listing, or gKASF6, represented by SEQ ID No 13 in the Sequence Listing, were designed and used together with a reverse primer gKASR6, represented by SEQ ID No 14 in the Sequence Listing, in this reaction.

A single PCR product of approximately 2 kb was resulted from the end-to-end PCR based on primer combinations of gKASF4-gKASR6 and gKASF6-gKASR6. The putative JbKASII cDNA was 1874 in length; it found to share high sequence similarity to other palm species such as *E. guineensis*. By using ORF Finder Software, it was observed that this JbKASII cDNA has an open reading frame (ORF) starts at A229TG or the 77$^{th}$ codon and ends at T1693AG or the 565$^{th}$ codon. Understandably, this JbKASII cDNA encodes for a 488 amino acid polypeptide, with 228 base pairs and 179 base pairs of 5'- and 3' untranslated region, respectively. Furthermore, it was also predicted that this full length JbKASII cDNA, preferably by an online-based prediction tool Compute pI/Mw, has a pI of approximately 7.08 and a molecular mass of approximately 52 kDa.

Based on in silico analysis, it was observed that JbKASII shows a significant similarity to KASII proteins isolated from various monocots and dicots. The amino acid sequence of the JbKASII shared a significant sequence identity to KASII homologs from plants, for example, *Elaeis guineensis* (97.5% identity), *Jatrophacurcas* (79.5% identity), *Arabidopsis thaliana* (77% identity), soybean (84.4% identity) and rice (83.7% identity).

FIG. 1 shows the ClustalW multiple sequence alignment of the amino acid sequence of JbKASII with KASII from *Elaeis guineensis, Elaeis oleifera* (Eo, Protein Accession No. ACQ41833), *Arabidopsis thaliana* (At, Protein Accession No. AAK69603), *Glycine max* (Gm, Protein Accession No. AAW88763), *Zea mays* (Zm, Protein Accession No. ACG25173) and *Jatrophacurcas* (Protein Accession No. ABJ90469). The amino sequence of JbKASII designated as SEQ ID NO. 1, as depicted in FIG. 1, is highly similar to that of the KASII homologs from other plants. Like other KASII homologs, JbKASII has a highly conversed active site triad motif, Cys299-His439-His 475 (in rectangular boxes as shown in FIG. 1). Two protein domains, namely N-terminal KASII domain and C-terminal KASII domain were found in the JbKASII amino acid sequence. Protein structure analysis suggested that enzymatic activity of the JbKASII proteins lies within these two protein domains. However, in contrast to most plant KASII homologs, JbKASII protein does not have a plastid targeting signal.

Referring to the phylogenetic tree of KAS homologs from various plant species, as depicted in FIG. 2, JbKASII protein is most related to KAS homologs from *E. oleifera* and *E. guineensis*. KASII homologs of *O. sativa, Z. mays*, and *H. vulgareare* diverged to form an independent branch of the phylogram, although they share the same ancestor with that of the *Jessenia bataua*. It, therefore, suggested that these sister groups may have different enzymatic efficiencies or substrate specificities. An out-group, which branches off at the base of the phylogeny and comprises of KAS homologs from *A. thaliana, P. frutescens* and *G. max* had also suggested that this Glade may be consisted of KASI protein, but not KASII protein.

Southern Blot Analysis

In one embodiment, three probes were employed to examine the genomic organization of JbKASII in *Jessenia* genome. These probes include KASII domain-specific probes that recognize sequences in the N-terminus and C-terminus to determine the number of JbKASII paralogs in the *Jessenia* genome and a 3'UTR-specific probe of approximately 200 bp in length for detecting the gene copy number of JbKASII.

KASII domain-specific probes for the C-terminus was amplified from the JbKASII cDNA clone using primers JkasCF, represented by SEQ ID No 15 in the Sequence Listing, and JkasCR, represented by SEQ ID No 16 in the Sequence Listing, whereas primers such as JkasNF, represented by SEQ ID No 17 in the Sequence Listing, and JkasNR, represented by SEQ ID No 18 in the Sequence Listing, were used to synthesis KASII domain-specific probe for the N-terminus. For the 3'UTR-specific probe synthesis, primers JK3UTRF, represented by SEQ ID No 19 in the Sequence Listing, and JK3UTRR, represented by SEQ ID No 20 in the Sequence Listing, were used.

The southern blot analysis of the present invention was carried out according to Sambrook et. al. *Jessenia* genomic DNA was digested with Dra1, EcoRV, HindIII, PvuII, StuI and XhoI (New England Biolabs USA) and resolved on a 0.8% agarose gel and subsequently being transferred to Nylon membranes (DuPont, USA). It was noted that these well-prepared probes were radio-labelled with 32P dCTP according to the Prime-It II Random Primer labeling Kit (Straragene, USA) user manual and hybridized overnight at 65° C., followed by 1× high-stringency wash.

Based on the Southern Blot analysis protocol as mentioned above, it was observed that, in FIG. 3, the JbKASII of the present invention is a single copy gene as only a single 2.75 kb band, and was detected in the DraI-digested DNA pool. Multiple bands were detected from the five DNA libraries generated using the restriction enzymes, namely DraI, EcoRV, HindIII, PvuII, StuI and XhoI, by the domain-specific probes. It, therefore, showed that rather than the KASII gene sequence, similar N-terminus and C-terminus KASII domains may also be found in other gene sequences of the *Jessenia* genome. It also suggested that, there are many paralogs in the *Jessenia* genome although it is a single copy gene that does not undergo gene duplication.

Expression of *Jessenia bataua* KASII (JbKASII) in *E. coli*

For gaining a better understanding of the biological function of the isolated JbKAS sequence, a His-tagged cDNA fusion of JbKASII was constructed and designated as pET32a: His-JbKASII-His. This pET32a:JbKASII-His was generated when a putative 1467 by ORF of JbKASII was amplified and cloned into a linearized pET-32a (+) vector (Novagen). Primers BamHI-KasF, represented by SEQ ID No 8 in the Sequence Listings, and Not1-KasR, represented by SEQ ID No 9 in the Sequence Listings, were employed to amplify the ORF. The expression cassette based on the ORF of JbKASII and the pET-32a (+) vector was subsequently transformed expressed by six different *E. coli* strains, preferably the BL21, BL21 (DE3), BL21 (DE3) pLysS, Rosetta-gami, Rosetta-gami B (DE3) pLysS and Origami (DE3). The preferred transformation was heat shock transformation.

In one preferred embodiment, proteins were extracted from the recombinants JbKASII expressed in *E. coli* cultures, particularly strains BL21, BL21(DE3), BL21(DE3)pLysS, Rosetta-gami B(DE3)pLysS (RpLyS), Origami (DE3) and Rosetta-gami (R) that had been incubated at 37° C., 28° C., and 22° C., respectively and followed by SDS-PAGE analysis to determine solubility thereof. Similar to most bacterial cell factories, recombinant proteins expressed in the *E. coli* cultures, particularly the only the Rosetta-gami B (DE3)pLysS and Rosetta-gami strains had failed to fold property and accumulated a copious amount of insoluble recombinants JbKASII at 37° C., as shown in FIG. 4A. These insoluble recombinant proteins, as understood by one skilled in the art, are non-functional inclusion bodies.

In addition, the fatty acid profile of *E. coli* cultures over-expressing JbKASII particularly the strain of Rosetta-gami B (DE3)pLysS incubated at about 22° C., as shown in FIG. 4b, had further supported that the misfolded proteins in the *E. coli* cultures over-expressing JbKASII is dysfunctional and are enzymatically inactive. The fatty acid composition of *E. coli* cultures over-expressing JbKASII was not significantly different from that of the un-induced control cultures. This observation could be explained that the lack of condensing activity of recombinant JbKASII or an overproduction of JbKASII in the *E. coli* cultures may inhibit fatty acid synthesis.

Expression of *Jessenia bataua* KASII (JbKASII) in *Arabidopsis thaliana*

Inconclusive results from the expression study of recombinant JbKASII in *E. coli* due to the inclusion bodies formation, as described previously, had encouraged the present inventors to express the JbKASII cDNA fusion constructs in *Arabidopsis thaliana*.

Two JbKASII Green Fluorescent Protein (GFP) fusion constructs were generated using Gateway recombination cloning technology (Invitrogen, US) for this expression study. These JbKASII GFP fusion constructs included p35S:GFP-JbKASII and p35S:JbKASII-GFP, which were characterized that having a GFP tagged to the C-terminal and N-terminal of the JbKASII protein, respectively.

In order to generate the N-terminal GFP fusion, approximately 1.5 kb cDNA of JbKASII was cloned as an attB1-JbKASII-stop-attB2 fragment into pDNOR211 to form pDNOR207-JbKASII-stop. The clone was subsequently sequenced and sub-cloned into the destination vector, p35S, to generate p35S:JbKASII-GFP. On the other hand, the p35S:GFP-JbKASII fusion constructs was preferably synthesis when the sequence pNOR207: JbKASII was sub-cloned into p35S vector. Both vectors were subjected to multiple restriction enzyme digestions to ensure that the insertion of the JbKASII cDNA was correctly oriented.

These well-prepared binary constructs were introduced into wild type *Arabidopsis*, particularly *Arabidopsis thaliana* (ecotype Columbia) based on *Agrobacterium*-mediated floral dipping method. The resultant transformants, which had a single locus insertion were subsequently selected and propagated to T3 generation, where seeds obtained therefrom were subjected to fatty acid analysis.

Prior to being subjected to a fatty acid analysis process, genotype of transgenic plant from generated from the T3 generation, which are either harboured the GFP-JbKASII transgene (C1) or the JbKASII-GFP transgene (C2) were determined by GFP-specific primers, preferably BamHI-GFP6-F, represented by SEQ ID No 10 in the Sequence Listing, and EcoRI-GFP6-R, represented by SEQ ID No 11 in the Sequence Listing, on a hydromycin-containing (15 µg/ml) MS medium.

Fatty acids were extracted from identified plants, particularly, seeds thereof, according to the following protocols: Approximately 0.1 g *Arabidopsis* seeds (about 5000 seeds) was initially incubated for roughly 1 hour at room temperature in about 7.5 ml extraction solvent consisting of water:(2%) HCl-acidified methanol:chloroform at a ratio of approximately 0.8:2:1. The suspension was spun down, and supernatant resulted therefrom was mixed with approximately 2.5 ml water and approximately 2.5 ml chloroform, to extract an organic fraction. The organic fraction was filtered using a silicone-treated IPS paper (Whatman, UK) to obtain fatty acids thereof.

The resultant fatty acids were then subjected to an esterification process, where approximately 2 ml toluene and approximately 2 ml 1% $H_2SO_4$-modified methanol were added to the fatty acids and allowed 2-hour incubation at 80° C. FAMEs were extracted by addition of 5% NaCl and 2 ml hexane to the esterified mixture, followed by collection of upper layer fraction after separation by centrifugation.

The FAMEs were concentrated under nitrogen gas streaming and re-constituted in approximately 0.5 ml hexane. The concentrated FAME samples were separated on a 30 m×0.25 mm DB WAX capillary column of a Perkin Elmer Clams 500 chromatograph. Preferably, fatty acid composition was expressed as relative means, which were calculated based on an external FAME standards mix, RM3 (Supelco, USA) run concurrently with each analysis.

FIG. 5A is a fatty acid profile of mature transgenic *Arabidopsis* seeds from 10 independent T3 lines, of which 7 lines were transgenic plants harboured the GFP-JbKASII transgene (designated as C1) and another 3 lines were transgenic plants harboured the JbKASII-GFP transgene (designated as C2). It is noted that the relative fatty acid composition from each line was compared to that of the untransformed wild type *Arabidopsis*. In the other words, fatty acid profile of each line was based on the ratios of transgenic: untransformed fatty acids.

As KASII homologs from the plant kingdom are known to elongate palmitic acid (C16:0) to strearic acid (C18:0). However, as shown in FIG. 5A, an unexpectedly decreased of fatty acids, particularly the stearic acid (C18:1) (in all independent lines) and the oleic acid (C18:0) (8 lines out of 10) in the p35S-JbKASII transgenic seeds, was observed. Interestingly, such reduction of the fatty acids C18:0 and C18:1 was accompanied by approximately 1 to 3-fold increased of C22:1 (8 lines out of 10). Furthermore, in lines C1-82 and C2-65, a significant elevation in C22:0 of up to approximately 5-fold was also observed. This observation, therefore, suggested that the over-expression of JbKASII in *Arabidopsis* results in accumulation of fatty acid C22:0 and C22:1 with fatty acids C18:0 and C18:1 as the substrates for this fatty acid biosynthesis process.

However, because of the phenotype of these transgenic plants was not expressed uniformly, the GFP transgene expression level in each transgenic plant was then determined using semi-quantitative RT-PCR. In a preferred embodiment, the semi-quantitative RT-PCR was performed using QuantiTect RT kit (Qiagen, Germany) according to the manufacturer's instructions. Briefly, approximately 1 µg RNA was converted to first strand cDNA in a 20 µl reaction containing about 1 µl RT primer mix. A serial dilution of the cDNA samples was prepared and used in subsequent PCR reactions with the following cycle conditions: 95° C., 30 seconds; 65° C., 30 seconds; 72° C., 60 seconds for 33 cycles. Arabodopsis Tubulin gene was employed as the loading control.

It was notice that the transgenic lines with a pronounced increment of fatty acid C22:1 and C22:0, for example, the line C1-43, C1-63, C1-82 and C2-65 did not show a high abundance of GFT transcripts as those transgenic lines with weak fatty acid phenotype did, as shown in FIG. 5A. It implied that the accumulation of the very long chain fatty acids, particularly C22:1 and C22:0 in transgenic plants is inversely related to the JbKASII transgene expression levels. Two possibilities may account for this finding: either JbKASII transcription was silenced and therefore, weakened its condensing activities, or the elongating activities of the JbKASII were met with bottleneck due to a rate-limiting factor.

Previous studies showed that the lack of acyl-CoA substrates in the acyl-CoA pool has restricted elongated C20 fatty acid synthesis, and hence disrupts acyl-CoA-dependent elongation. This implies that proper channeling of the desaturated C18:0 and C18:1 into endoplasmic recticulumacyl-CoA pool is critical for VLCFA accumulation. Therefore, accumulation of VLCFA can be regulated not merely by varying expression levels of the JbKASII transgene; however, it can be achieved by coordinating expression of other genes involved in the relevant biosynthesis pathway, desaturases and acyltransferases, for example.

Although there was no significant increase of fatty acid, particularly the C18:0 in the p35S-JbKASII transgenic *Arabidopsis* seeds, however, the presence of KASII paralogs with conserved KAS domains in the *Jessenia* genome was believed that might lead to synthesis of VLCFA at the expense of fatty acids, C16:0. Accordingly, a functional complementation test to determine whether the JbKASII transgene complements with *Arabidopsis* KASII mutant, fatty acid biosynthesis 1 (fab1) was performed. Two fab1 mutants, namely fab1-1 and fab1-2 were characterized for this complementation test. The fab1-1 is an EMS mutant with a L337F substitution in the active site of KASII while the fab1-2 is a T-DNA mutant with T-DNA insertion in the sixth introns of FAB1 locus. Both mutant genes showed deficiency in C16:0 condensing activities due to dysfunctional KASII enzymes. As a result, a high level of C16:0 accumulated in seeds and leaves would be observed.

Difficulties in germinating embryo lethal fab1-1 seeds had suggested to transform heterozygous FAB/fab1-2 with a single transgene insertion, either p35S: GFP-JbKASII or p35S:JbKASII-GFP, generating FAB1/fab1-2 transformants. These transformants were subsequently recovered by genotyping and propagated to T3 generation. Fatty acid profiling was performed on 6 independent homozygous transgenic lines from the T3 generation. These 6 independent lines included 5 lines harboured p35S: GFP-JbKASII (designated as F1) and 1 line harboured p35S: GFP-JbKASII-GFP (designated as F2).

As illustrated in FIG. 5B, there was no significant reduction of fatty acids, C18:0 and C18:1 observed in these independent homozygous JbKASII transgenic lines. However, these lines had shown an appreciation of C22:1. For example, the line F2-41 had approximately 3.6-fold increase of C22:1. Notably, this transgenic line, F2-41, had weak transgene expression of JbKASII, and the GPT transcripts could barely be detected. Furthermore, no consistent reduction in C16:0 was observed in the FAB1/fab1-2 plants complemented with JbKASII compared to that of the untransformed FAB1/fab1-2 plants. This could be explained that the fab1-2 may not functionally be complemented by the JbKASII.

To confirm that the fab1-2 is not complemented by JbKASII, up to 100 individuals segregating for FAB1/fab1-2 were genotyped. As the *Arabidopsis* KASII knock-out mutant, fab1-2 is an embryo lethal and segregates at a distorted 2 (FARO: 1 (FAB/fab1-2) ratio. Therefore, complementation with wild-type copy of AtKASII could restore the 1(FAB1):2(FAB1/fab1-2): 1 (fab1-2) segregation. No homozygous fab1-2/fab1-2 plants were recovered from the genotyping, and thus confirming that the JbKASII does not complement with the fab1-2 or the JbKASII fails to rescue fab1-2. The previous hypothesis stated that the JbKASII might involved in palmitic acid (C16:0) elongation was therefore rejected and confirmed that the JbKASII functionally resembles keto-acyl-CoA synthase (KCS). Both KSC and JbKASII share the same substrate specificity; they preferentially elongate stearic and oleic acid, but not palmitic acid.

Although the present invention has been described with reference to the preferred embodiments and examples thereof, it is apparent to those skilled in the art that a variety of modifications and changes may be made without departing from the scope of the present invention which is intended to be defined by the appended claims.

What is claimed is:

1. A recombinant DNA construct comprising a nucleic acid fragment encoding a His-tagged protein having fatty acid elongation activity, wherein said protein comprises the amino acid sequence as depicted in SEQ ID NO.1 and the His-tag.

2. A recombinant DNA construct as claimed in claim 1, wherein said nucleic acid fragment is isolated from the plant *Jessenia bataua*.

3. A recombinant DNA construct as claimed in claim 1, wherein said protein is a β-ketoacyl ACP synthase (II) (KASII).

4. A recombinant DNA construct as claimed in claim 1, wherein said amino acid sequence includes Cys299-His439-His 475.

5. A recombinant DNA construct as claimed in claim 1, wherein said isolated nucleic acid fragment encodes a 488-amino acid polypeptide and the His tag, and comprises approximately 228 base pairs of a 5' untranslated region and approximately 179 base pairs of a 3' untranslated region.

6. A recombinant DNA construct as claimed in claim 1, wherein the protein enhances the production and the accumulation of very long chain fatty acids, at the expense of stearic acid (C18:0) and oleic acid (C18:1).

7. A recombinant DNA construct as claimed in claim 1, wherein the protein produces very long chain fatty acids when expressed in a plant cell and said very long chain fatty acids include arachidic acid (C20:0) and erucic acid (C22:1).

8. Plants containing the recombinant DNA construct of claim 1, wherein the protein is heterologous.

9. Oil obtained from the plants of claim 8 containing the recombinant DNA construct as claimed in claim 1, wherein said oil comprises said recombinant DNA construct.

10. A method of enhancing the production and accumulation of very long chain fatty acids in a transgenic plant comprising the steps:
    transforming a plant cell with a recombinant DNA construct comprising a nucleic acid fragment encoding a heterologous protein having fatty acid elongation activity, wherein said protein has the amino acid sequence as depicted in SEQ ID NO.1;
    cultivating the transformed plant cell under a condition where expression of the foreign nucleic fragment is permitted; and
    generating the transgenic plant from the plant cell.

11. A method of enhancing the production and accumulation of very long chain fatty acids in a transgenic plant, comprising transforming a plant cell with a recombinant DNA construct comprising a nucleic acid fragment encoding a protein comprising SEQ ID NO.1, wherein said protein is a β-ketoacyl ACP synthase (II) (KASII), which elongates stearic acid (C18:0) and oleic acid (C18:1) to yield very long chain fatty acids including arachidic acid (C20:0) and erucic acid (C22:1), wherein production of very long chain fatty acids in the plant is enhanced.

* * * * *